(12) United States Patent
Monchi et al.

(10) Patent No.: US 7,315,821 B2
(45) Date of Patent: Jan. 1, 2008

(54) SYSTEM AND METHOD FOR HEALTH CARE INFORMATION PROCESSING BASED ON ACOUSTIC FEATURES

(75) Inventors: Rie Monchi, Kyoto (JP); Masakazu Asano, Neyagawa (JP); Hirokazu Genno, Hirakata (JP)

(73) Assignee: Sanyo Electric Co., Ltd., Osaka (JP)

( * ) Notice: Subject to any disclaimer, the term of this patent is extended or adjusted under 35 U.S.C. 154(b) by 897 days.

(21) Appl. No.: 10/356,331

(22) Filed: Jan. 31, 2003

(65) Prior Publication Data
US 2003/0182117 A1    Sep. 25, 2003

(30) Foreign Application Priority Data
Jan. 31, 2002   (JP)   ............................. 2002-024823
Jan. 31, 2002   (JP)   ............................. 2002-024826

(51) Int. Cl.
*G10L 21/00* (2006.01)
(52) U.S. Cl. .................................... 704/273; 379/88.13
(58) Field of Classification Search ................ 704/273; 379/88.13
See application file for complete search history.

(56) References Cited

U.S. PATENT DOCUMENTS

| | | | | |
|---|---|---|---|---|
| 4,493,947 A | * | 1/1985 | Loveless | 379/40 |
| 5,897,616 A | * | 4/1999 | Kanevsky et al. | 704/246 |
| 6,044,134 A | * | 3/2000 | De La Huerga | 379/88.08 |
| 6,071,236 A | * | 6/2000 | Iliff | 600/300 |
| 6,161,090 A | * | 12/2000 | Kanevsky et al. | 704/246 |
| 6,480,826 B2 | * | 11/2002 | Pertrushin | 704/270 |
| 6,826,540 B1 | * | 11/2004 | Plantec et al. | 705/10 |
| 6,858,006 B2 | * | 2/2005 | MacCarter et al. | 600/300 |
| 6,873,268 B2 | * | 3/2005 | Lebel et al. | 340/870.16 |

(Continued)

FOREIGN PATENT DOCUMENTS

JP    H2-39268    2/1990

(Continued)

OTHER PUBLICATIONS

Acoustical properties of speech as indicators of depression and suicidal risk France, D.J.; Shiavi, R.G.; Silverman, S.; Silverman, M.; Wilkes, M.; Biomedical Engineering, IEEE Transactions on vol. 47, Issue 7, Jul. 2000 pp. 829-837.*

(Continued)

*Primary Examiner*—Michael Opsasnick
(74) *Attorney, Agent, or Firm*—Darby & Darby

(57) ABSTRACT

A question as to the physical condition and a question as to the feeling are asked, answers are accepted by voice, acoustic features are extracted from the answer to the question as to the physical condition, and character string information is extracted from the answer to the question as to the feeling. A correlation between the acoustic features and the character string information is set, and character string information is identified from a newly accepted acoustic feature, thereby performing feeling presumption. Feeling is presumed from the voice in response to the subject's severalty and changes in the subject's age and physical condition. A medical examination by interview on the mental condition is performed on the subject by voice output and voice input, and the subject's mental condition is diagnosed based on the contents of the subject's answer and analysis of the answer by voice.

26 Claims, 20 Drawing Sheets

U.S. PATENT DOCUMENTS

2002/0082665 A1* 6/2002 Haller et al. .................. 607/60
2004/0016437 A1* 1/2004 Cobb et al. ................. 131/270

FOREIGN PATENT DOCUMENTS

| JP | H5-12023    | 1/1993 |
| -- | ----------- | ------ |
| JP | 8-117210    | 5/1996 |
| JP | 2000-245718 | 9/2000 |
| JP | 2001-215993 | 8/2001 |
| JP | 2002-7568   | 1/2002 |
| WO | WO-01/39584 | 6/2001 |

OTHER PUBLICATIONS

Speech under stress conditions: overview of the effect on speech production and on system performance Steeneken, H.J.M.; Hansen, J.H.L.; Acoustics, Speech, and Signal Processing, 1999. ICASSP '99. Proceedings., 1999 IEEE International Conference on vol. 4, Mar. 15-19, 1999 pp. 2079-2082 vol. 4.*

Classification of speech under stress based on features derived from the nonlinear Teager energy operator Guojun Zhou; Hansen, J.H.L.; Kaiser, J.F.; Acoustics, Speech, and Signal Processing, 1998. ICASSP '98. Proceedings of the 1998 IEEE International Conference on vol. 1, May 12-15, 1998 pp. 549-552 vol. 1.*

T. Moriyama, H. Saito and S. Ozawa, Evaluation of the Relation between Emotional Concepts and Emotional Parameters in Speech, Dep't. of EE, Keio University, Electrical Information-D-II, vol. J82-D-II, No. 4, pp. 703-311, Apr. 1999.

* cited by examiner

FIG. 3A

| DATE | SOUND PRESSURE | PITCH FREQUENCY | PITCH VARIABILITY | DURATION | JITTER | FEELING SCORE | PRESUMED VALUE |
|---|---|---|---|---|---|---|---|
| Dec.1 | 75 | 150 | 18 | 0.2 | 5 | 60 | — |
| Dec.2 | 50 | 120 | 30 | 0.5 | 8 | 30 | — |
| Dec.3 | 98 | 175 | 15 | 0.3 | 3 | 80 | — |

FIG. 3B

| QUESTION ID | CONTENTS |
|---|---|
| M01 | WHAT IS THE SCORE OF YOUR FEELING TODAY WHEN RATED ON A SCALE OF 100? |
| F01 | ARE YOU UNBEARABLY HUNGRY? |
| F02 | DO YOU HAVE A HEADACHE? |

FIG. 19

| DATE | SCORE OF FEELING | PROCESSING PROGRAM | FEELING OF ROBOT | SCORE BY ROBOT |
|---|---|---|---|---|
| Jan. 8 | 50 POINTS | "Cheer up" | "I wonder" | 70 POINTS |
| Jan. 9 | 100 POINTS | Nothing | "Full marks!" | 90 POINTS |
| Jan. 10 | 70 POINTS | "Word chain game" | "Will be okay tomorrow?" | 80 POINTS |
| ... | ... | ... | ... | ... |

SYSTEM AND METHOD FOR HEALTH CARE INFORMATION PROCESSING BASED ON ACOUSTIC FEATURES

BACKGROUND OF THE INVENTION

The present invention relates to an information processing method, an information processing system and an information processing apparatus for presuming information accompanying a voice based on acoustic features extracted from the voice, a health care terminal apparatus for aiding the subject's health care, and a recording medium on which a computer program for implementing these is recorded.

Methods are known such that the feeling accompanying an input voice is presumed by analyzing the voice by use of an information processing apparatus such as a personal computer or a voice processing apparatus. Conventionally, two methods described below have principally been known:

One method is to identify a character string corresponding to the input voice by performing voice recognition on the voice and presume the accompanying feeling based on the contents of the character string. According to this method, by determining whether or not the contents of the identified character string coincide with the vocabulary information prepared as a vocabulary indicating feelings, one feeling is identified from among feelings classified into approximately 10 kinds such as joy, anger, sorrow, surprise and pleasure.

The other method is to presume the degree (intonation) of the feeling by analyzing the waveform of the input voice and extracting feature amounts such as the intensity (sound pressure level), the pitch frequency and the duration of the voice. According to this method, first, reference values of the feature amounts such as the sound pressure level, the pitch frequency and the duration are set as a preparation step prior to feeling presumption. As the reference values, for example, the average values of the feature amounts of populations such as adult men, adult women and children are used. When feeling presumption is performed, the subject's voice is newly taken, and the feature amounts are extracted by analyzing the waveform of the voice. Then, the extracted feature amounts are compared with the reference values of the population to which the subject belongs, and the degree of the subject's feeling is presumed based on the result of the comparison.

However, according to the method presuming the feeling based on the contents of the identified character string, the degree of the feeling cannot be presumed, and according to the method presuming the degree of the feeling from the feature amounts (the sound pressure level, the pitch frequency and the duration) of the voice, it is difficult to presume what feeling the presumed degree of the feeling corresponds to.

Moreover, when the average values of adult men, adult women and children are used as the reference values of the feature amounts, the subject's severalty cannot be reflected. Further, voices generally vary by aging and according to the subject's physical condition, and frequently vary according to the time when the voice is taken. Therefore, it is desirable that the feeling can be appropriately presumed so that aging, the subject's physical condition and the time when the voice is taken are reflected.

By the way, various robots have been developed that copy after the shapes and actions of pet animals, imaginary animals and the like so as to capture the subject's affection. These robots are designed to output voices to the subject through a speaker, capture the subject's voices through a microphone, take images with a CCD camera and move movable parts.

It is pursued to use this kind of robots, for example, for home health care of elderly persons. In this case, the robot obtains and stores information on the subject's health condition including results of a medical examination by interview such as the subject's physical condition and feeling obtained by performing a medical examination by interview and measurement data such as the temperature and the blood pressure measured by the subject himself, and periodically transmits the stored health condition information to a medical institution such as a hospital or a public health center. Moreover, when the elderly person's condition changes suddenly, the robot informs a predetermined emergency hospital of that. Further, a robot has recently been developed that includes a sensor for measuring the subject's health condition such as a pulse rate sensor so that the subject's pulse rate can be taken when the subject touches the part of the sensor.

These health care robots which aid the subject having no family living together or having no caregiver in his health care are convenient, particularly, to elderly persons living alone. However, conventionally, the focus has been frequently placed on changes in the subject's physical condition and sufficient care has not been taken of the subject's mental condition. Moreover, although the subject cares for the robot with interest for a while after the introduction of the robot when the robot is new to the subject, the subject who has to repeat predetermined processings every day gradually loses interest in the robot as time passes by.

BRIEF SUMMARY OF THE INVENTION

The present invention is made in view of such circumstances, and an object thereof is to provide an information processing method, an information processing system and an information processing apparatus capable of easily presuming the contents and the degree of information accompanying a voice uttered by a subject from the voice, by outputting two pieces of question information correlated with each other, accepting the answers to the outputted pieces of question information by voice, extracting character string information from the voice associated with one of the answers, extracting feature information associated with acoustic features from the voice associated with the other of the answers, setting a correlation between the character string information and the feature information, and when a voice associated with the answer to question information is newly accepted, identifying character string information correlated with the feature information associated with the acoustic features extracted from the accepted voice based on the feature information and the set correlation, and a recording medium on which a computer program is recorded for implementing the information processing system and the information processing apparatus.

Yet another object of the present invention is to provide an information processing method, an information processing system and an information processing apparatus capable of easily presuming the contents of the feeling and the degree of the feeling based on a voice uttered by the subject by one of the pieces of question information being question information on the mental condition and the other being question information on the physical condition.

Still another object of the present invention is to provide an information processing method, an information processing system and an information processing apparatus capable of appropriately presuming information so that the time when the voice is taken is reflected by determining whether it is a predetermined period or not when an answer to question information is accepted by voice and setting a correlation between stored character string information and feature information only when it is the predetermined period.

Still another object of the present invention is to provide an information processing method, an information processing system and an information processing apparatus capable of making a plurality of pieces of feature information to be reflected in presumption by calculating a feature amount characterizing each of stored character string information and feature information and setting a correlation between the character string information and the feature information by multivariate analysis using the calculated feature amounts.

Still another object of the present invention is to provide a health care terminal apparatus capable of improving the subject's mental condition by performing for the subject an appropriate processing in accordance with the result of the diagnosis of the subject's mental condition, and a recording medium on which a computer program for implementing the health care terminal apparatus is recorded.

Still another object of the present invention is to provide a health care terminal apparatus capable of being used over a long period of time by maintaining the subject's motivation to use the apparatus by selecting at random the contents of the processing performed for the subject so that use over a long period of time does not tire the subject, and a recording medium on which a computer program for implementing the health care terminal apparatus is recorded.

According to an information processing method of a first aspect, in an information processing method in which by an information processing system comprising storing means for storing question information, output means for outputting the question information and accepting means for accepting a voice, the question information stored in the storing means is outputted, an answer to the outputted question information is accepted by voice, acoustic features associated with the accepted voice are extracted, and information accompanying the voice is presumed based on the extracted acoustic features; a first piece of question information and a second piece of question information previously stored in the storing means and correlated with each other are outputted from the output means, answers to the outputted first and second pieces of question information are accepted by voice, character string information is extracted from a voice associated with the accepted answer to the first piece of question information, at least one piece of feature information associated with the acoustic features is extracted from a voice associated with the accepted answer to the second piece of question information, the extracted character string information and feature information are stored so as to be associated with each other, a correlation between the stored character string information and feature information is set, and when a voice associated with an answer to the second piece of question information is newly accepted by the accepting means, character string information correlated with at least one piece of feature information associated with the acoustic features extracted from the accepted voice is identified based on the piece of feature information and the set correlation.

According to an information processing method of a second aspect, in the first aspect, one of the first and the second pieces of question information is question information on a mental condition and the other of the first and the second pieces of question information is question information on a physical condition.

According to an information processing method of a third aspect, in the first or the second aspect, when the answer to the first or the second piece of question information is accepted by voice, it is determined whether it is a predetermined period or not, and only when it is the predetermined period, the correlation between the stored character string information and feature information is set.

According to an information processing method of a fourth aspect, in any of the first to the third aspects, a feature amount characterizing each of the stored character string information and feature information is calculated, and the correlation is set by multivariate analysis using the calculated feature amounts.

According to an information processing system of a fifth aspect, in an information processing system comprising: storing means for storing question information; output means for outputting the question information stored in the storing means; and means for accepting a voice, in which an answer to the question information outputted from the output means is accepted by voice, and information accompanying the accepted voice is presumed based on acoustic features extracted from the accepted voice, the following are provided: means for outputting a first piece of question information and a second piece of question information previously stored in the storing means and correlated with each other; means for accepting answers to the outputted first and second pieces of question information by voice; character string information extracting means for extracting character string information from a voice associated with the accepted answer to the first piece of question information; feature information extracting means for extracting at least one piece of feature information associated with the acoustic features from a voice associated with the accepted answer to the second piece of question information; means for storing the extracted character string information and feature information so as to be associated with each other; and means for setting a correlation between the stored character string information and feature information, and when a voice associated with an answer to the second piece of question information is newly accepted by the accepting means, character string information correlated with at least one piece of feature information associated with the acoustic features extracted from the accepted voice is identified based on the piece of feature information and the set correlation.

According to an information processing system of a sixth aspect, in an information processing system comprising a first information processing apparatus and a second information processing apparatus connected through a communication network, the first information processing apparatus comprising: storing means for storing question information; and transmitting means for transmitting the question information stored in the storing means, the second information processing apparatus comprising: means for receiving question information transmitted through the communication network; means for accepting an answer to the received question information by voice; and means for transmitting voice information associated with the accepted voice, the first information processing apparatus presuming information accompanying the voice information received through the communication network based on acoustic features extracted from the voice information, the second information processing apparatus comprises: means for receiving, through the network, a first piece of question information and a second piece of question information previously stored in the storing means of the first information processing apparatus and correlated with each other; means for outputting the received first and second pieces of question information; means for accepting answers to the outputted first and second pieces of question information by voice; and means for transmitting voice information associated with the accepted voice, the first information processing apparatus comprises: character string information extracting means for extracting character string information from voice information associated with the received answer to the first piece of question information; feature information extracting means for extracting at least one piece of feature information associated with the acoustic features from voice information associated with the received answer to the second piece of question information; means for storing the extracted character string information and feature information so as to be associated with each other; and means for setting a correlation between the stored character string information and feature information, and when voice information associated with an answer to the second piece of question information is newly received from the second information processing apparatus, character string information correlated with at least one piece of feature information associated with the acoustic features extracted from the received voice information is identified based on the piece of feature information and the set correlation.

According to an information processing system of a seventh aspect, in the fifth or the sixth aspect, one of the first and the second pieces of question information is question information on a mental condition and the other of the first and the second pieces of question information is question information on a physical condition.

According to an information processing system of an eighth aspect, in any of the fifth to the seventh aspects, means is provided for determining whether it is a predetermined period or not when the answer to the first or the second piece of question information is accepted by voice, and only when it is the predetermined period, the correlation between the stored character string information and feature information is set.

According to an information processing system of a ninth aspect, in any of the fifth to the eighth aspects, a feature amount characterizing each of the stored character string information and feature information is calculated, and the correlation is set by multivariate analysis using the calculated feature amounts.

According to an information processing apparatus of a tenth aspect, in an information processing apparatus comprising: storing means for storing question information; output means for outputting the question information stored in the storing means; and means for accepting a voice, in which an answer to the question information outputted from the output means is accepted by voice, and information accompanying the accepted voice is presumed based on acoustic features extracted from the accepted voice, the following are provided: means for outputting a first piece of question information and a second piece of question information previously stored in the storing means and correlated with each other; means for accepting answers to the outputted first and second pieces of question information by voice; character string information extracting means for extracting character string information from a voice associated with the accepted answer to the first piece of question information; feature information extracting means for extracting at least one piece of feature information associated with the acoustic features from a voice associated with the accepted answer to the second piece of question information; means for storing the extracted character string information and feature information so as to be associated with each other; and means for setting a correlation between the stored character string information and feature information, and when a voice associated with an answer to the second piece of question information is newly accepted by the accepting means, character string information correlated with at least one piece of feature information associated with the acoustic features extracted from the accepted voice is identified based on the piece of feature information and the set correlation.

According to an information processing apparatus of an eleventh aspect, in an information processing apparatus being connectable to a communication network, having means for receiving voice information, and presuming information accompanying the received voice information based on acoustic features extracted from the received voice information, the following are provided: means for receiving answers to a first piece of question information and a second piece of question information correlated with each other as voice information through the communication network; character string information extracting means for extracting character string information included in the voice information associated with the received answer to the first piece of question information from the voice information; feature information extracting means for extracting at least one piece of feature information associated with the acoustic features from voice information associated with the received answer to the second piece of question information; means for storing the extracted character string information and feature information so as to be associated with each other; and means for setting a correlation-between the stored character string information and feature information, and when voice information associated with an answer to the second piece of question information is newly received, character string information correlated with at least one piece of feature information associated with the acoustic features extracted from the received voice information is identified based on the piece of feature information and the set correlation.

According to an information processing apparatus of a twelfth aspect, in the tenth or the eleventh aspect, one of the first and the second pieces of question information is question information on a mental condition and the other of the first and the second pieces of question information is question information on a physical condition.

According to an information processing apparatus of a thirteenth aspect, in any of the tenth to the twelfth aspects, means is provided for determining whether it is a predetermined period or not when the answer to the first or the second piece of question information is accepted by voice, and only when it is the predetermined period, the correlation between the stored character string information and feature information is set.

According to an information processing apparatus of a fourteenth aspect, in any of the tenth to the thirteenth aspects, a feature amount characterizing each of the stored character string information and feature information is calculated, and the correlation is set by multivariate analysis using the calculated feature amounts.

According to an information processing apparatus of a fifteenth aspect, in any of the tenth to the fourteenth aspects, the feature information extracting means comprises at least one of detecting means for detecting a sound pressure of inputted voice information, detecting means for detecting a pitch frequency of the inputted voice information, detecting means for detecting duration of the inputted voice information and detecting means for detecting jitter of the inputted voice information.

According to an information processing apparatus of a sixteenth aspect, in any of the tenth to the fifteenth aspects, means is further provided for outputting appropriate information in accordance with the identified character string information.

According to a computer-readable recording medium of a seventeenth aspect, in a computer-readable recording medium on which a computer program is recorded that comprises a step of causing a computer to extract acoustic features associated with inputted voice information and presume information accompanying the voice information based on the extracted acoustic features, a computer program is recorded that comprises: a step of causing the computer to output a first piece of question information and a second piece of question information correlated with each other; a step of causing the computer to accept answers to the outputted first and second pieces of question information by voice information; a step of causing the computer to extract character string information from the voice information associated with the accepted answer to the first piece of question information; a step of causing the computer to extract at least one piece of feature information associated with the acoustic features from the voice information associated with the accepted answer to the second piece of question information; a step of causing the computer to store the extracted character string information and feature information so as to be associated with each other; a step of causing the computer to set a correlation between the stored character string information and feature information; and a step of causing the computer to identify, when voice information associated with an answer to the second piece of question information is newly accepted, character string information correlated with at least one piece of feature information associated with the acoustic features extracted from the accepted voice information, based on the piece of feature information and the set correlation.

According to the present invention, two pieces of question information correlated with each other are outputted, the answers to the outputted pieces of question information are accepted by voice, character string information is extracted from the voice associated with one of the answers, feature information associated with acoustic features is extracted from the voice associated with the other of the answers, a correlation between the extracted character string information and feature information is set, and when a voice associated with an answer to question information is newly accepted, character string information correlated with the feature information associated with the acoustic features extracted from the accepted voice is identified based on the feature information and the set correlation. Consequently, for example, when one of the pieces of question information is question information on the subject's feeling and the other is a question as to the subject's physical condition, the subject's feeling can be presumed by asking the subject to answer to the question as to the physical condition. In particular, by asking the subject to answer to the question as to the feeling with an evaluation of the subject's specific feeling and setting a correlation between the evaluation and the acoustic features extracted from the answer to the question as to the physical condition, the kind of the feeling and the degree (intonation) of the feeling can be quantatively presumed only from the answer by voice to the question as to the physical condition.

Moreover, according to the present invention, one of the pieces of question information is question information on the mental condition and the other is question information on the physical condition. Consequently, the contents of the feeling and the degree of the feeling can be easily presumed based on the voice uttered by the subject.

Further, according to the present invention, when the answer to the question information is accepted by voice, it is determined whether it is a predetermined period or not, and only when it is the predetermined period, the correlation between the stored character string information and feature information is set. Consequently, a period (for example, approximately one week) during which voice information is collected for setting the above-mentioned correlation can be provided at the start of use of the information processing system of the present invention. Moreover, to perform feeling presumption in appropriate consideration of aging, the subject's physical condition and the like, the correlation can be updated, for example, every month. Consequently, feeling presumption can be performed over a long period of time, and presumption errors can be reduced.

Further, according to the present invention, a feature amount characterizing each of the stored character string information and feature information and the correlation between the character string information and the feature information is set by multivariate analysis using the calculated feature amounts. Consequently, since feeling presumption can be performed by use of a plurality of feature amounts, even when an influence such as the subject's physical condition is exerted on a specific acoustic feature, the influence can be minimized.

A health care terminal apparatus of an eighteenth aspect comprises: means for performing a medical examination by interview on a mental condition; means for diagnosing the mental condition based on a result of the medical examination by interview; means for storing a plurality of processing programs for improving the mental condition; and means for selecting one processing program from among the stored processing programs and executing the selected program.

According to a health care terminal apparatus of a nineteenth aspect, a health care terminal aiding a subject's health care comprises: means for outputting a voice to perform a medical examination by interview on a mental condition on a subject; means for inputting the subject's answer by voice in the medical examination by interview; diagnosing means for diagnosing the subject's mental condition based on the subject's answer by voice; means for storing a plurality of processing programs for improving the subject's mental condition; and means for selecting one processing program from among the stored processing programs and executing the selected program.

According to a health care terminal apparatus of a twentieth aspect, in the eighteenth or the nineteenth aspect, the processing program is selected at random.

According to a health care terminal apparatus of a twenty-first aspect, in the nineteenth or the twentieth aspect, analyzing means is provided for analyzing the subject's voice when the subject answers in the medical examination by interview, and the diagnosing means diagnoses the subject's mental condition based on a content of the subject's answer in the medical examination by interview and a result of the voice analysis by the analyzing means.

According to a recording medium of a twenty-second aspect, in a computer-readable recording medium on which a computer program causing a computer to aid health care is recorded, a computer program is recorded that comprises: a step of causing the computer to perform a medical examination by interview on a mental condition; a step of causing the computer to diagnose the mental condition based on a result of the medical examination by interview; and a step of causing the computer to select one processing program from among a plurality of stored processing programs for improving the mental condition and execute the selected program.

According to a recording medium of a twenty-third aspect, in the twenty-second aspect, the computer program comprises a step of causing the computer to select the processing program at random.

According to a recording medium of a twenty-fourth aspect, in the twenty-second or the twenty-third aspect, the computer program comprises a step of causing the computer to analyze a voice when an answer is made in the medical examination by interview, and a step of causing the computer to diagnose the mental condition based on a content of the answer in the medical examination by interview and a result of the voice analysis.

According to the present invention, the mental condition is diagnosed based on the result of the medical examination by interview on the mental condition, one processing program is selected from among a plurality of prepared processing programs (such as outputting encouraging words, proposing breathing for relaxation, and proposing playing a game), and the selected processing program is executed. Consequently, an appropriate processing can be performed in accordance with the subject's mental condition, so that the subject's mental condition can be improved.

According to the present invention, a medical examination by interview on the mental condition is performed on the subject by voice output and voice input, the subject's mental condition is diagnosed based on the contents of the subject's answer, one processing program is selected from among a plurality of prepared processing programs, and the selected processing program is executed. Consequently, an appropriate processing can be performed in accordance with the subject's mental condition, so that the subject's mental condition can be improved.

According to the present invention, the processing program executed for the subject is selected at random. Consequently, it never occurs that the same processing is always performed for the subject, so that the subject never loses interest and health care can be continued over a long period of time.

According to the present invention, voice analysis is performed on the subject's answer in the medical examination by interview, and the subject's mental condition is diagnosed based on the result of the analysis and the contents of the answer in the medical examination by interview. Consequently, the subject's mental condition can be more precisely diagnosed.

The above and further objects and features of the invention will more fully be apparent from the following detailed description with accompanying drawings.

BRIEF DESCRIPTION OF THE SEVERAL VIEWS OF THE DRAWINGS

FIG. 3A is a conceptual view showing an example of an analysis database;

FIG. 3B is a conceptual view showing an example of a question information database;

FIG. 19 shows an example of a home page generated by the health care robot; and

DETAILED DESCRIPTION OF THE INVENTION

Hereinafter, the present invention will be concretely described based on the drawings showing embodiments thereof.

First Embodiment

Figure 1:
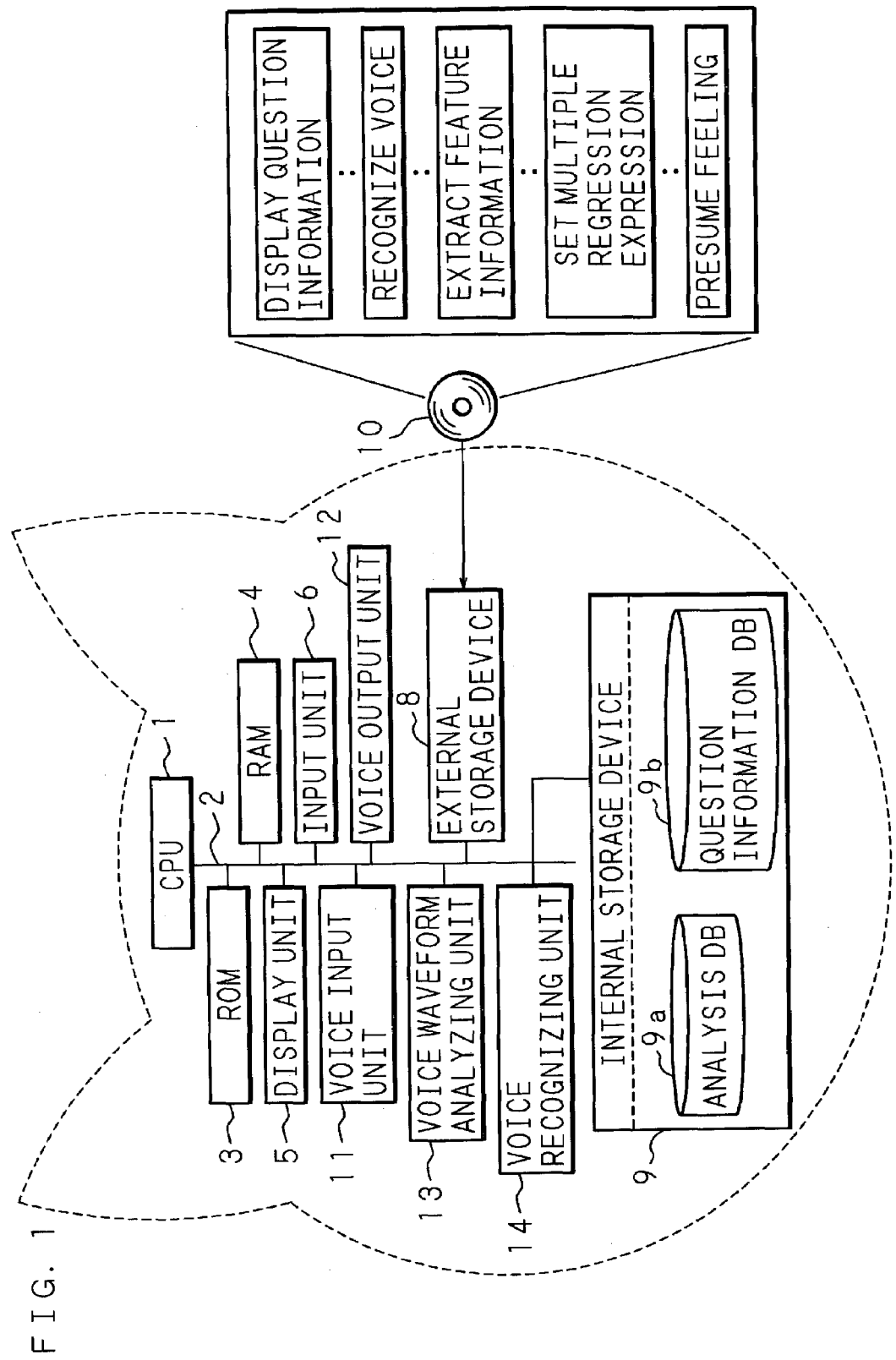
FIG. 1 is a block diagram showing the internal structure of a feeling presuming apparatus embodying the information processing apparatus of the present invention.

FIG. 1 is a block diagram showing the internal structure of a feeling presuming apparatus embodying an information processing apparatus of the present invention. The feeling presuming apparatus according to the present embodiment is, for example, a "cat-type" care robot having a voice input unit 11 such as a microphone. The feeling presuming apparatus asks questions as to a physical condition and a mental condition, accepts answers to the questions through the voice input unit 11, and analyzes the waveform of the accepted voice to thereby presume the feeling accompanying the voice.

In FIG. 1, reference numeral 1 represents a CPU. The CPU 1 is connected to hardware units described later through a bus 2, and controls the units according to a control program stored in a ROM 3. A RAM 4 comprises an SRAM, a flash memory or the like, and stores data generated when the control program stored in the ROM 3 is executed.

A display unit 5 is a display such as a liquid crystal display for displaying question information on the physical and the mental conditions. The question information is stored in a question information database (question information DB) 9b provided in an internal storage device 9. When the question information is stored in the question information database 9b as voice data, the question information may be outputted from a voice output unit 12 such as a speaker. An input unit 6 is provided with various button switches for controlling the operation of the feeling presuming apparatus.

A voice waveform analyzing unit 13 analyzes the voice waveform converted into an electric signal by the voice input unit 11, and calculates feature amounts associated with acoustic features such as the sound pressure, the pitch frequency and the duration. A voice recognizing unit 14 performs voice recognition on the voice information inputted through the voice input unit 11, and converts the voice information into character string information. The character string information obtained by the conversion is evaluated as described later, and the evaluated value is stored in an analysis database (analysis DB) 9a. The internal storage device 9 comprises a storage device such as a hard disk. Part of the storage area thereof is used as the above-described question information database 9b and the analysis database 9a storing the result of the analysis by the voice waveform analyzing unit 13. The internal storage device 9 accesses various databases as required to perform information storage and reading.

An external storage device 8 comprises a reader reading out a computer program and data from a portable recording medium 10 such as a memory card on which the computer program of the present invention and data such as question information are recorded. The computer program and the data being read out are stored in the internal storage device 9. The computer program stored in the internal storage device 9 is read into the RAM 4 and executed by the CPU 1, whereby the apparatus operates as a feeling presuming apparatus.

Figure 2A:
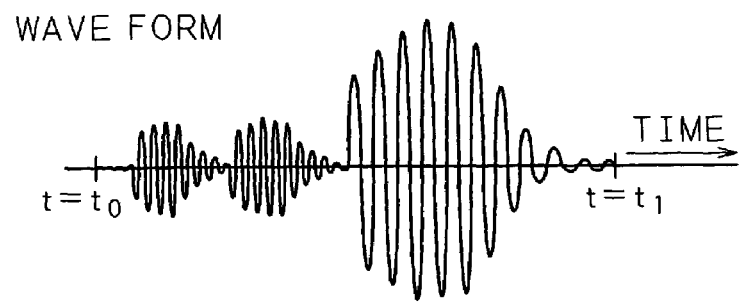
FIG. 2A shows the waveform of voice information inputted through a voice input unit.
Figure 2B:
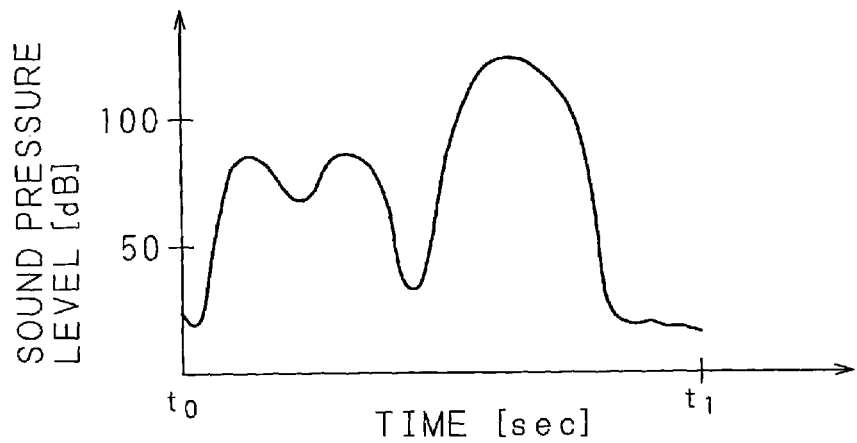
FIGS. 2B and 2C are graphs showing examples of variations with time of feature amounts extracted by a voice waveform analyzing unit.
Figure 2C:
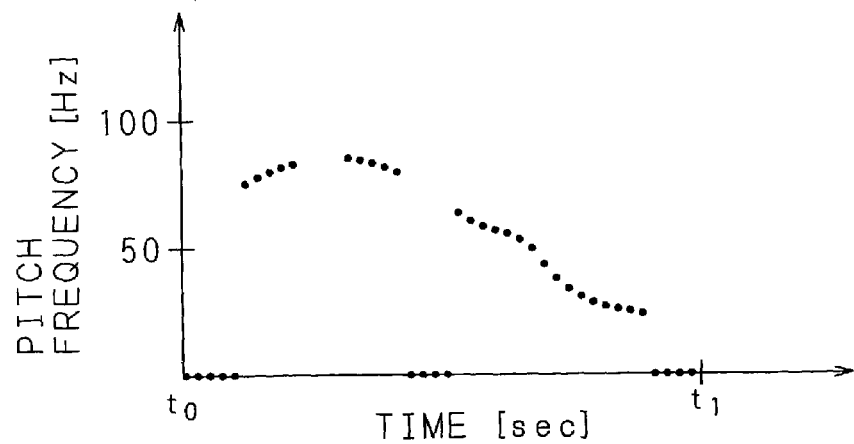

FIGS. 2A to 2C are graphs showing examples of variations with time of the waveform of the voice information inputted through the voice input unit 11 and feature amounts extracted by the voice waveform analyzing unit 13. The example of FIG. 2A shows the waveform of the voice information when the subject says "No" as the answer to a question. The waveform of the voice information inputted through the voice input unit 11 is analyzed by the voice waveform analyzing unit 13, so that a variation with time of the sound pressure level as shown in the graph of FIG. 2B and a variation with time of the pitch frequency as shown in the graph of FIG. 2C are obtained.

The sound pressure level and the pitch frequency are functions that vary with time as shown in FIGS. 2B and 2C. As the feature amounts characterizing these, the maximum value, the average value, the median value and the like in the duration of the voice ($t_1$-$t_0$ in FIG. 2) are adopted. For example, as the feature amount of the sound pressure level, the average value in the duration of the voice is taken, and as the feature amount of the pitch frequency, the maximum value in the duration of the voice is adopted. As described above, it is predetermined which of the maximum value, the average value, the median value and the like are adopted as the feature amounts associated with the acoustic features such as the sound pressure level and the pitch frequency.

The voice waveform analyzing unit 13 is capable of analyzing the variability with time of the pitch frequency, the duration of the voice and jitter corresponding to voice hoarseness as well as the variation with time of the sound pressure level and the variation with time of the pitch frequency mentioned above. The feature amounts obtained by the analysis and calculation are stored in the analysis database 9a so as to be associated with the date of the analysis.

It is known that the sound pressure level, the pitch frequency, the variability with time of the pitch frequency, the duration of the voice, the jitter and the like mentioned above are generally dependent on the subject's feeling. When the subject is in good health and the subject's feeling is in good condition, the sound pressure level, the pitch frequency and the variability with time of the pitch frequency increase. It is known that the duration of the voice and the jitter which frequently differ among subjects generally decrease when the subject's feeling is in good condition. On the contrary, it is known that the sound pressure level, the pitch frequency and the variability with time of the pitch frequency decrease and the duration of the voice and the jitter increase when the subject is in an ill temper and the subject's feeling is in bad condition.

As described above, it is known that the acoustic features of the voice are closely related to the subject's feeling. According to the present invention, in order that the severalty such as aging and the subject's physical condition and the time when feeling presumption is performed are reflected in the result of the presumption, feeling presumption is not performed based on only the above-mentioned feature amounts associated with the acoustic features but is performed in the following manner: First, a physical examination by interview asking the physical condition and a mental examination by interview asking the feeling are performed for a predetermined period (for example, one week) to collect preliminary data of the voice information. Then, the feature amounts calculated from the answer in the physical examination by interview are associated with the contents of the answer in the mental examination by interview, and feeling presumption is performed from the answer in the physical examination by interview performed after the end of the above-mentioned period (hereinafter, referred to as data collection period). For example, approximately one week in the beginning of each month is set as the data collection period for collecting preliminary data of the voice information, and the feature amounts calculated from the answer in the physical examination by interview are associated with the contents of the answer in the mental examination by interview.

FIG. 3A is a conceptual view showing an example of the analysis database 9a. In collecting the preliminary data, when the physical examination by interview is performed, the date of the analysis of the voice information, and the feature amounts associated with the sound pressure level (sound pressure), the pitch frequency, the variability of the pitch frequency (pitch variability: For example, a difference (Hz) between the maximum pitch frequency and the minimum pitch frequency in a speech), the duration and the jitter are stored so as to be associated with each other. The jitter is an index of instability in a larynx waveform and is measured as a variation of fundamental period. Concretely, the jitter(%) is obtained as the following expression wherein i-th and (i+1)-th fundamental periods are Y(i) and Y(i+1).

$$\text{Jitter} = (|Y(i) - Y(i+1)| \times 100) \div [\{Y(i) + Y(i+1)\} \div 2]$$

From the mental examination by interview, a feeling score is calculated and stored so as to be associated with the feature amounts. Here, the feeling score expresses whether the feeling, the sentiment and the mood are good or bad as a score. The score expressing the best feeling (sentiment, mood) is 100, and the score expressing the worst feeling (sentiment, mood) is 0. Further, when the physical examination by interview is performed for feeling presumption after the preliminary data is collected, the feature amounts and the presumed value of the feeling score are stored so as to be associated with each other.

FIG. 3B is a conceptual view showing an example of the question information database 9b. In the question information database 9b, question IDs for identifying the question information and the contents of the question information are stored so as to be associated with each other. In the example of FIG. 3B, a piece of question information such as "What is the score of your feeling today when rated on a scale of 100?" is stored so as to be associated with a question ID "M01" as a question asked in the mental examination by interview, and pieces of question information such as "Are you unbearably hungry?", "Do you have a headache?" and so on are stored so as to be associated with question IDs "F01," "F02" and so on, respectively, as questions asked in the physical examination by interview.

These pieces of question information are outputted when the preliminary data is collected or when feeling presumption is performed. The question information may be outputted as character information through the display unit 5 of the feeling presuming apparatus or may be outputted as voice information from the voice output unit 12. The answers to the question information are inputted as voice information through the voice input unit 11. The answer in the mental examination by interview is converted into a character string by voice recognition processing, and the part which is the nucleus of the answer, that is, the score provided by the subject himself in the case of the above-mentioned question, is extracted. In the analysis database 9a, the extracted score is stored as the feeling score. In the physical examination by interview, the voice information associated with the answer is converted into digital form by an AD converter or the like, and the digitized voice waveform is temporarily stored in the RAM 4. Then, only the waveform of the part which is the nucleus of the answer, that is, the part corresponding to "Yes" or "No" is extracted from the stored voice waveform, and the waveform is analyzed. The feature amounts associated with the acoustic features obtained by the analysis are stored in an appropriate storage area of the analysis database 9a.

To facilitate the analysis of the waveform of the voice information and the voice recognition, it is desirable that the question information be one whose answers can be predicted to some extent. Like the above-mentioned examples, the questions in the mental examination by interview are ones asking the subject to express his feeling as a score, and questions in the physical examination by interview are yes-no questions. In particular, in the physical examination by interview, when the questions are unified to ones asking if the subject is in poor or serious physical condition, since the probability that the subject answers "NO" is high, the analysis of the waveform of the voice information is further facilitated.

Figure 4A:
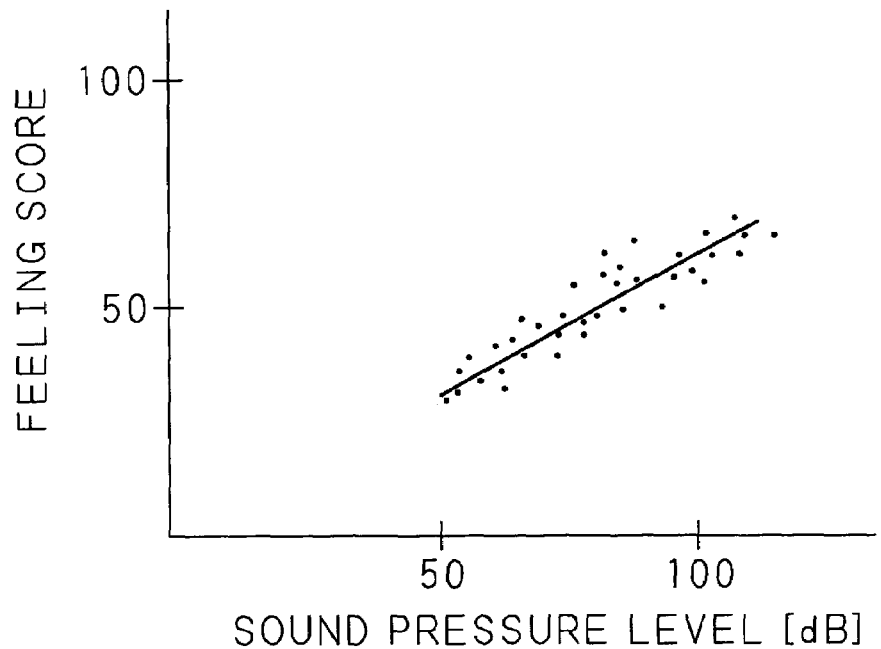
FIGS. 4A and 4B are graphs showing examples of the distributions of feeling scores with respect to feature amounts calculated from acoustic features.
Figure 4B:
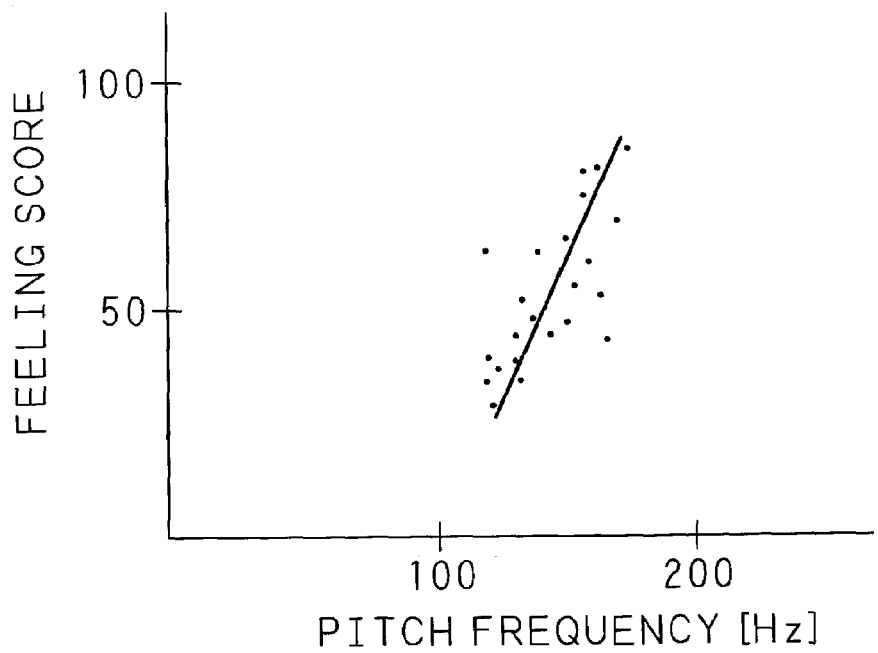

FIGS. 4A and 4B are graphs showing examples of the distributions of feeling scores with respect to feature amounts calculated from acoustic features. FIG. 4A is a graph showing the distribution of feeling scores with respect to the sound pressure level. FIG. 4B is a graph showing the distribution of feeling scores with respect to the pitch frequency. As mentioned above, the sound pressure level tends to be high when the subject's feeling is in good condition, and the subject should provide a high score as his feeling score. Therefore, a score distribution is exhibited such that the feeling score tends to increase as the sound pressure level increases as shown in FIG. 4A. The same applies to the pitch frequency. The pitch frequency tends to be high when the subject's feeling is in good condition, and the subject should provide a high score as his feeling score. Therefore, a score distribution is exhibited such that the feeling score tends to increase as the pitch frequency increases as shown in FIG. 4B. Moreover, although not shown, there is some tendency between each of the acoustic indices of the variability with time of the pitch frequency, the duration of the voice and the jitter and the feeling score, and the distribution of the feeling score can be graphed.

By setting mathematical models expressing these score distributions, the feeling score can be easily presumed from the feature amounts. The simplest one of the above-mentioned mathematical models is a regression line expressing the feeling score by one kind of feature amount. The regression line can be obtained by use of the method of least squares.

In collecting the voice information, the speed at which the voice is transmitted differs, for example, between when the air is dry and when the air includes much moisture. Therefore, it is considered that changes of the outside air are apt to largely affect the duration of the voice and the pitch frequency. On the other hand, it is considered that the sound pressure level which is the absolute amount at a given time is less likely to be affected by the outside air. When the subject is in poor physical condition because of having a cold, this affects particularly the pitch frequency and the jitter. Therefore, when a mathematic model is set from one kind of feature amount for feeling presumption, feeling presumption cannot be always performed with a high degree of precision.

Therefore, according to the present embodiment, to minimize the influence of the outside air and the influence of the subject's physical condition and the like, a mathematical model expressing a score distribution is set by multivariate analysis by use of all of the above-mentioned five kinds of feature amounts.

Hereinafter, a case will be described in which a mathematical model expressing the distribution of the feeling score is set by use of multiple regression analysis which is one kind of the multivariate analysis. In the multiple regression analysis, a relationship between an objective variable y and explanatory variables $x_1, x_2, x_3, \ldots$ is determined by the multiple regression analysis. In the present embodiment, the feeling score calculated from the answer in the mental examination by interview is taken as the objective variable y, and the five feature amounts calculated from the acoustic features of the answer in the physical examination by interview are taken as the explanatory variables $x_1, x_2, \ldots, x_5$. Here, the explanatory variables $x_1, x_2, \ldots, x_5$ correspond to the sound pressure level, the pitch frequency, the variability with time of the pitch frequency, the duration of the voice and the jitter, respectively.

When a question in the mental examination by interview and a question in the physical examination by interview are respectively performed n times, a number n of objective variables $(y_1, y_2, \ldots, y_n)$ and a total of a number n×5, a number n for each feature amount, of explanatory variables $(x_{11}, x_{12}, \ldots, x_{n5})$ are obtained. These relationships are expressed by a number n of linear equations like (1) shown below.

$$y_1 = \alpha + \beta_1 x_{11} + \beta_2 x_{12} + \ldots + \beta_5 x_{15}$$

$$y_2 = \alpha + \beta_1 x_{21} + \beta_2 x_{22} + \ldots + \beta_5 x_{25}$$

$$y_n = \alpha + \beta_1 x_{n1} + \beta_2 x_{n2} + \ldots + \beta_5 x_{n5} \qquad (1)$$

Here, $\alpha$ is a constant, and $\beta i$ (i=1, ..., 5) are multiple regression coefficients.

When the presumed least square value of α, βi (i=1, ..., 5) is expressed by a, bi (i=1, ..., 5), using these coefficients, a multiple regression expression of y with respect to $x_1, x_2, ..., x_5$ is obtained as shown in (2).

$$Y = a + b_1 x_1 + b_2 x_2 + ... + b_5 x_5 \quad (2)$$

The method of obtaining the multiple regression expression is well known. By calculating a, bi such that the square sum of the differences (residuals) between observed values yj (j=1, ..., n) and presumed values Yj (j=1, ..., n) is minimum, the multiple regression expression can be obtained. Here, the observed values yj are $y_1, ..., y_n$ in the expressions (1) given above, and the presumed values Yj are values obtained by substituting the number 5×n of feature amounts $x_{11}, x_{13}, ..., x_{n5}$ into the expression (2). The multiple regression expression obtained by substituting the calculated constant a and multiple regression coefficients bi (i=1, ..., 5) into the expression (2) is the mathematical model to be obtained, and by assigning newly obtained feature amounts to $x_1, x_2, ..., x_5$, the presumed value Y of the feeling score is obtained.

While the mathematical model of the score distribution is set by use of the multiple regression analysis in the present embodiment, discriminant analysis and correspondence analysis may be used as well as the multiple regression analysis.

Figure 5:
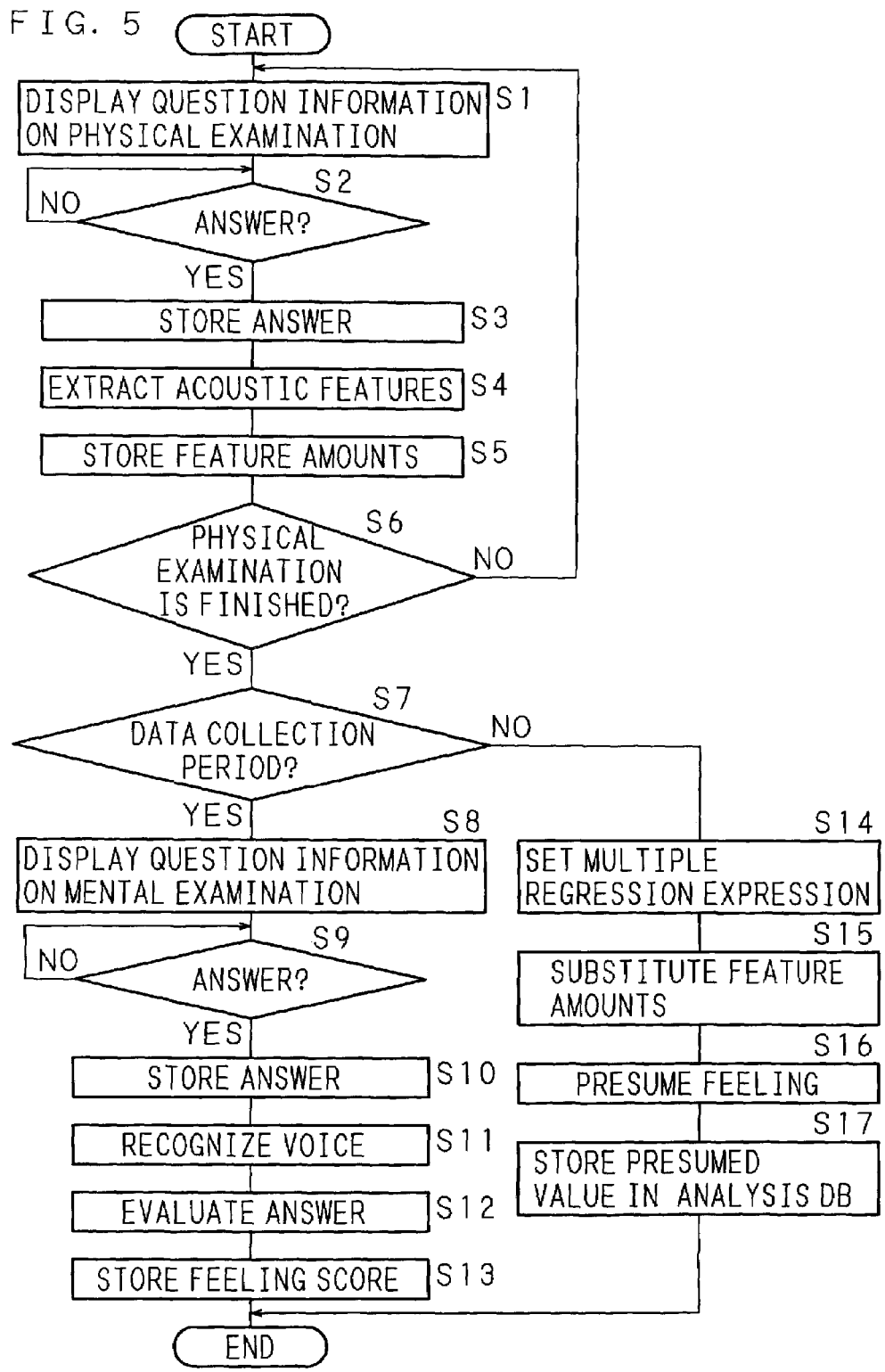
FIG. 5 is a flowchart showing the processing procedure of the feeling presuming apparatus.

FIG. 5 is a flowchart showing the processing procedure of the feeling presuming apparatus. The feeling presuming apparatus first displays question information on the physical examination by interview on the display unit 5 (step S1). The displayed question information may be one selected at random from the question information database 9b or one selected in the order of the question IDs. Moreover, the question information may be outputted by voice from the voice output unit 12.

Then, it is determined whether an answer by voice to the displayed question information is accepted or not (step S2). When no answer is accepted (S2: NO), the process waits until an answer is accepted. When an answer is accepted (S2: YES), the answer is stored as voice information (step S3). Then, the voice waveform analyzing unit 13 analyzes the waveform of the voice information stored at step S3, and extracts the acoustic features (step S4). Then, the feature amounts such as the sound pressure level and the pitch frequency obtained by analyzing the waveform are stored into the analysis database 9a (step S5).

Then, whether the physical examination by interview is finished or not is determined by determining whether answers to all the pieces of question information are accepted or not (step S6). When the physical examination by interview is not finished (S6: NO), the process returns to step S1. When the physical examination by interview is finished (S6: YES), it is determined whether it is the data collection period or not (step S7). When it is the data collection period (S7: YES), question information on the mental examination by interview is displayed on the display unit 5 (step S8). The question information may be outputted by voice from the voice output unit 12 without displayed on the display unit 5.

Then, it is determined whether an answer by voice to the displayed question information is accepted or not (step S9). When no answer is accepted (S9: NO), the process waits until an answer is accepted. When an answer is accepted (S9: YES), the answer is stored as voice information (step S10). Then, the voice recognizing unit 13 performs voice recognition on the voice information stored at step S10, and converts the voice information into a character string (step S11). The part which is the nucleus of the answer is extracted from the character string obtained by the conversion, and the answer is evaluated (step S12). In the mental examination by interview, a question such as "What is the score of your feeling today when rated on a scale of 100?" is asked as mentioned above. Therefore, the score of the subject's feeling provided by the subject himself can be adopted as the evaluation of the answer. Then, the evaluation of the answer is stored as the feeling score into the analysis database 9a (step S13).

When it is determined at step S7 that it is not the data collection period (S7: NO), the multiple regression expression is set (step S14). When the multiple regression expression is set, the multiple regression analysis is used by using the sound pressure level, the pitch frequency, the variability with time of the pitch frequency, the duration of the voice and the jitter already stored in the analysis database 9a as explanatory variables and using the feeling score as the objective variable. Then, the feature amounts newly extracted at step S4 are substituted into the set multiple regression expression (step S15), and the presumed value of the feeling score is obtained, thereby performing feeling presumption (step S16). The presumed value of the feeling score is stored in the analysis database 9a (step S17).

While in the present embodiment, the subject himself provides a score evaluating his feeling in the mental examination by interview and the score is adopted as the feeling score, it may be performed to prepare some yes-no questions like in the case of the physical examination by interview and calculate the feeling score according to the number of times the subject answers "Yes" and the number of time the subject answers "No." While in the present embodiment, a "cat-type" care robot is described as an example of the feeling presuming apparatus, the present invention is not limited to care robots, but it is to be noted that personal computers, workstations and the like including a voice input unit such as a microphone or being connectable as an external input apparatus may be used.

Second Embodiment

In the present embodiment, a method will be described of correcting the presumed value of the feeling score when there is a difference between the feeling score obtained from the answer in the mental examination by interview and the feeling score presumed by the multiple regression analysis.

Figure 6:
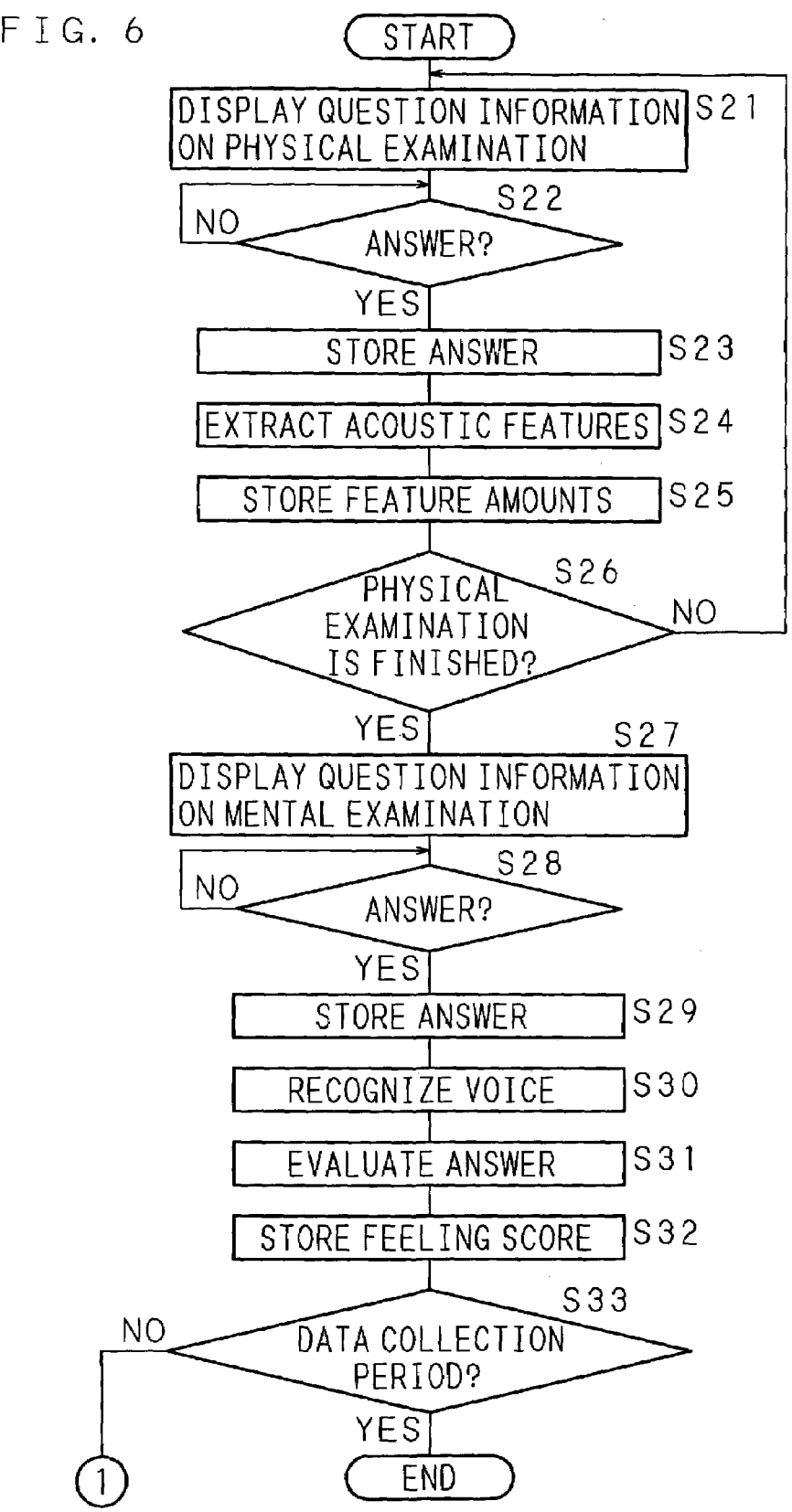
FIG. 6 is a flowchart showing the processing procedure of the feeling presuming apparatus.
Figure 7:
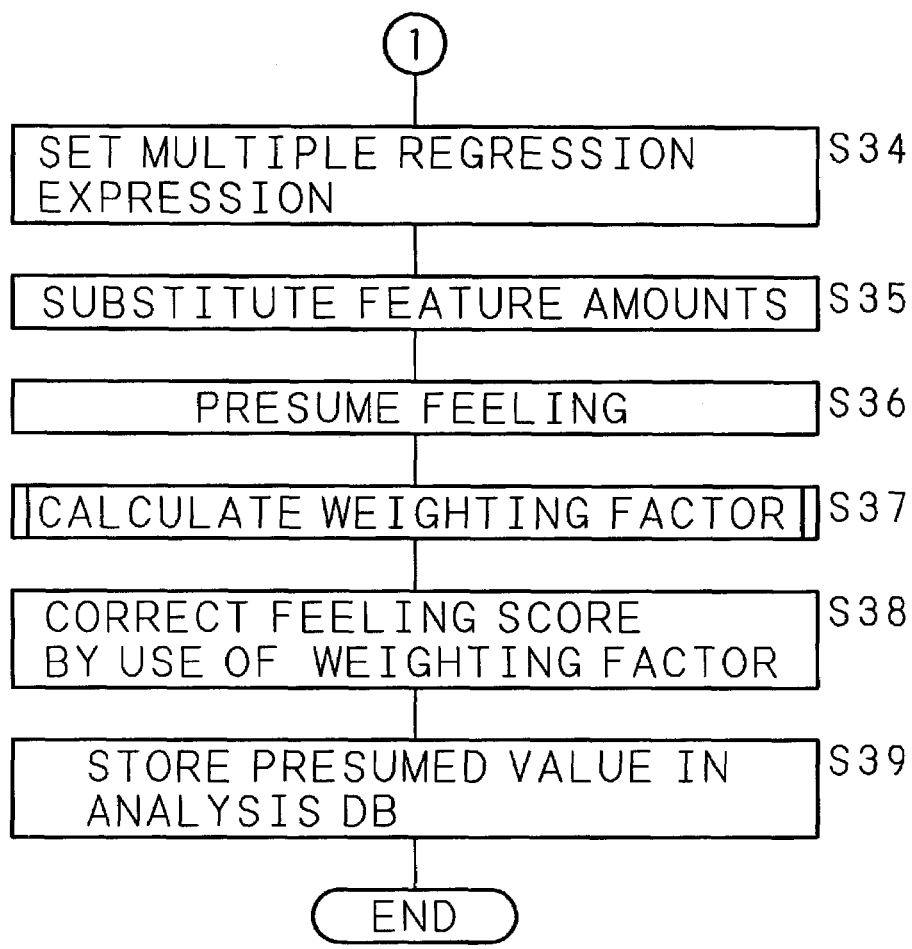
FIG. 7 is a flowchart showing the processing procedure of the feeling presuming apparatus.

Description of the structure of the feeling presuming apparatus which is similar to that of the first embodiment is omitted. FIGS. 6 and 7 are flowcharts showing the processing procedure of the feeling presuming apparatus according to the present embodiment. The feeling presuming apparatus first displays question information on the physical examination by interview on the display unit 5 (step S21). The displayed question information may be one selected at random from the question information database 9b or one selected in the order of the question IDs. Moreover, the question information may be outputted by voice from the voice output unit 12.

Then, it is determined whether an answer by voice to the displayed question information is accepted or not (step S22). When no answer is accepted (S22: NO), the process waits until an answer is accepted. When an answer is accepted (S22: YES), the answer is stored as voice information (step S23). Then, the voice waveform analyzing unit 13 analyzes the waveform of the voice information stored at step S23, and extracts the acoustic features (step S24). Then, the feature amounts such as the sound pressure level and the pitch frequency obtained by the waveform analysis are stored into the analysis database 9a (step S25).

Then, whether the physical examination by interview is finished or not is determined by determining whether answers to all the pieces of question information are accepted or not (step S26). When the physical examination by interview is not finished (S26: NO), the process returns to step S21. When the physical examination by interview is finished (S26: YES), question information on the mental examination by interview is displayed on the display unit 5 (step S27). The question information may be outputted by voice from the voice output unit 12 without displayed on the display unit 5.

Then, it is determined whether an answer by voice to the displayed question information is accepted or not (step S28). When no answer is accepted (S28: NO), the process waits until an answer is accepted. When an answer is accepted (S28: YES), the answer is stored as voice information (step S29).

Then, the voice recognizing unit 14 performs voice recognition on the voice information stored at step S29, and converts the voice information into a character string (step S30). The part which is the nucleus of the answer is extracted from the character string obtained by the conversion, and the answer is evaluated (step S31). In the mental examination by interview, a question such as "What is the score of your feeling today when rated on a scale of 100?" is asked as mentioned above. Therefore, the score of the subject's feeling provided by the subject himself can be adopted as the evaluation of the answer. Then, the evaluation of the answer is stored as the feeling score into the analysis database 9a (step S32). Then, it is determined whether it is the data collection period or not (step S33). When it is determined that it is the data collection period (S33: YES), the process ends.

When it is determined at step S33 that it is not the data collection period (S33: NO), the multiple regression expression is set (step S34). When the multiple regression expression is set, the multiple regression analysis is performed by using the sound pressure level, the pitch frequency, the variability with time of the pitch frequency, the duration of the voice and the jitter already stored in the analysis database 9a as explanatory variables and using the feeling score as the objective variable. Then, the feature amounts newly extracted at step S24 are substituted into the set multiple regression expression (step S35), and the presumed value of the feeling score is obtained, thereby performing feeling presumption (step S36). Then, a weighting factor between the presumed feeling score and the feeling score obtained from the evaluation of the answer in the mental examination by interview is calculated by a method described later (step S37). Then, the feeling score is corrected by use of the calculated weighting factor (step S38), and the corrected value of the feeling score is stored into the analysis database 9a (step S39).

Figure 8:
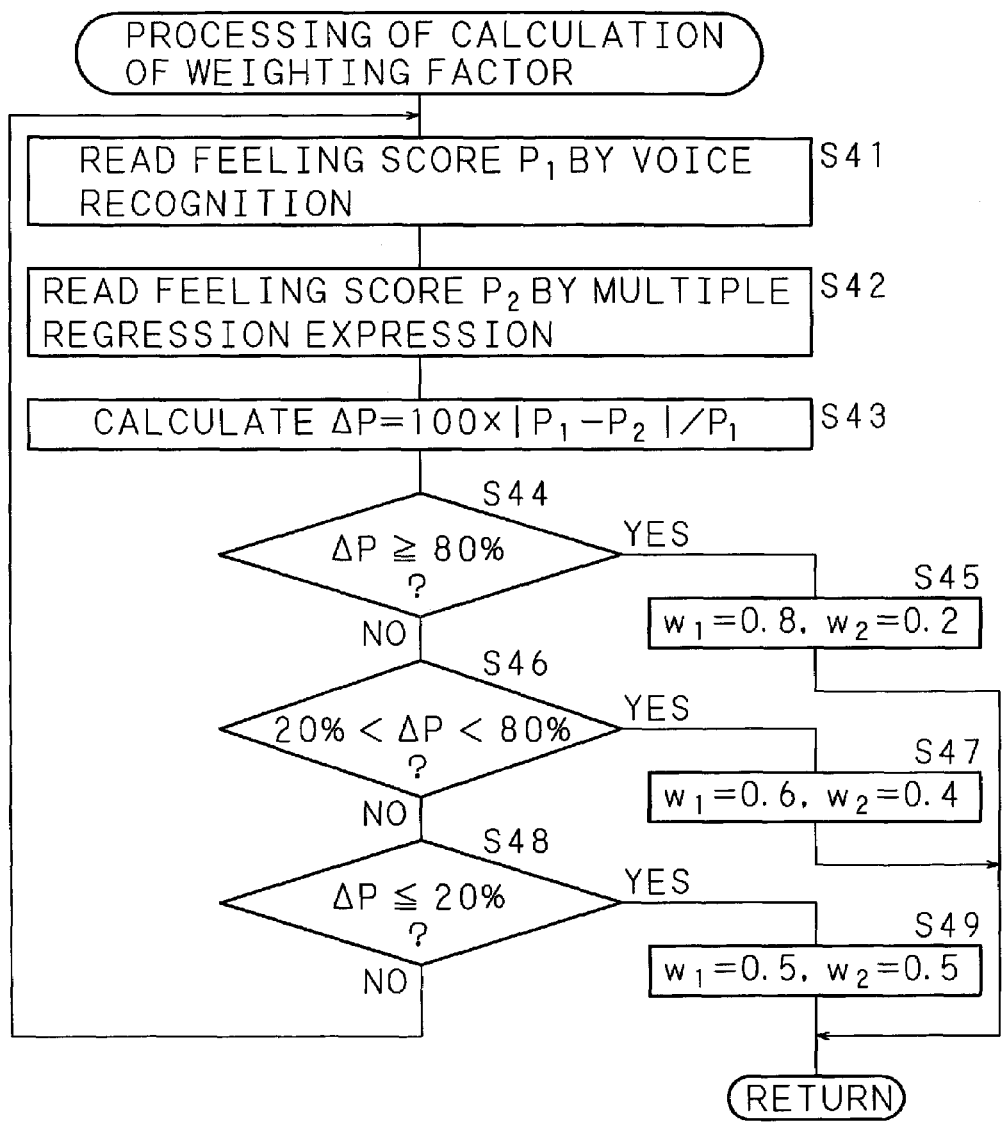
FIG. 8 is a flowchart showing the processing of calculation of a weighting factor.

FIG. 8 is a flowchart showing the processing of the calculation of the weighting factor. First, a feeling score Pi obtained by performing voice recognition on the answer in the mental examination by interview is read in (step S41). Then, a feeling score P2 presumed by use of the multiple regression expression is read in (step S42).

Then, the ratio $\Delta P$ (=100×|$P_1$−$P_2$|/$P_1$) of the difference between the two feeling scores is calculated (step S43). Then, it is determined whether the ratio $\Delta P$ of the difference is not less than 80% or not (step S44). When the ratio $\Delta P$ of the difference is not less than 80% (S44: YES), a weighting factor $w_1$ by which $P_1$ is multiplied is set to 0.8, and a weighting factor $w_2$ by which P2 is multiplied is set to 0.2 (step S45).

When the ratio $\Delta P$ of the difference is lower than 80% (S44: NO), it is determined whether or not the ratio $\Delta P$ of the difference is lower than 80% and higher than 20% (step S46). When the ratio $\Delta P$ of the difference is lower than 80% and higher than 20% (S46: YES), the weighting factor $w_1$ by which $P_1$ is multiplied is set to 0.6, and the weighting factor $w_2$ by which P2 is multiplied is set to 0.4 (step S47).

When the ratio $\Delta P$ of the difference does not satisfy the condition of step S46 (S46: NO), it is determined whether the ratio $\Delta P$ of the difference is not more than 20% or not (step S48). When the ratio $\Delta P$ of the difference is not more than 20% (S48: YES), the weighting factor $w_1$ by which $P_1$ is multiplied is set to 0.5, and the weighting factor $w_2$ by which P2 is multiplied is set to 0.5 (step S49). When the ratio $\Delta P$ of the difference does not satisfy the condition of step S48 (S48: NO), the process returns to step S41.

Third Embodiment

While the presumed value of the feeling score is stored in the analysis database 9a in the above-described embodiments, when the feeling is evaluated based on the feeling score, it is necessary to set reference values for each subject. This is because it is impossible to provide common reference values since some subjects always provide high feeling scores and others always provide low scores.

Figure 9:
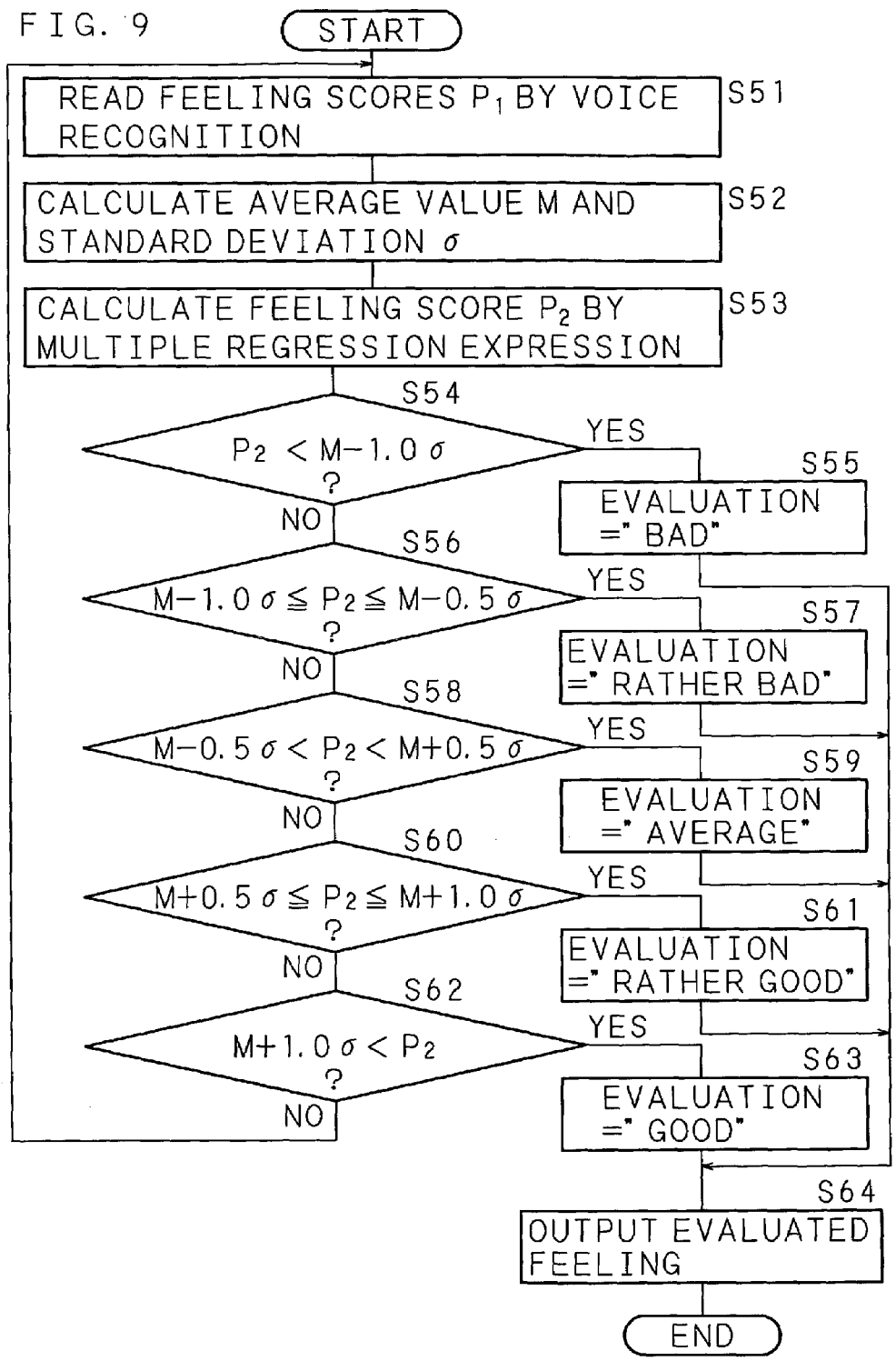
FIG. 9 is a flowchart showing the processing procedure when reference values for feeling evaluation are set for each subject.

FIG. 9 is a flowchart of the processing procedure when reference values for feeling evaluation are set for each subject. First, the feeling presuming apparatus reads in the feeling scores $P_1$ provided by a specific subject from the analysis database 9a (step S51), and calculates the average value M and the standard deviation σ of the feeling scores $P_1$ being read in (step S52). Then, the feeling score P2 is calculated by the multiple regression expression in a manner similar to the above-described one (step S53).

Then, it is determined whether the feeling score P2 is lower than M-1.0 σ or not (step S54). When the feeling score P2 is lower than M-1.0 σ (S54: YES), the evaluation of the feeling is "bad" (step S55). When the feeling score P2 is not less than M-1.0 σ (S54: NO), it is determined whether the feeling score P2 is not less than M-1.0 σ and not more than M-0.5σ (step S56). When the feeling score P2 is not less than M-1.0 σ and not more than M-0.5 σ (S56: YES), the evaluation of the feeling is "rather bad" (step S57).

When the feeling score P2 does not satisfy the condition of step S56 (S56: NO), it is determined whether or not the feeling score P2 is higher than M-0.5 σ and lower than M+0.5 σ (step S58). When the feeling score P2 is higher than M-0.5σ and lower than M+0.5σ (S58: YES), the evaluation of the feeling is "average" (step S59). When the feeling score P2 does not satisfy the condition of step S58 (S58: NO), it is determined whether the feeling score P2 is not less than M+0.5σ and not more than M+1.0σ (step S60). When the feeling score P2 is not less than M+0.5σ and not more than M+1.0σ (S60: YES), the evaluation of the feeling is "rather good" (step S61).

When the feeling score P2 does not satisfy the condition of step S58 (S60: NO), it is determined whether the feeling score P2 is higher than M+1.0σ or not (step S62). When the feeling score P2 is higher than M+1.0σ (S62: YES), evaluation of the feeling is "good" (step S63). When the feeling score P2 is not more than M+1.0σ (S62: NO), the process returns to step S51. Then, the evaluated feeling is outputted, for example, by being displayed on the display unit 5 of the feeling presuming apparatus (step S64).

Fourth Embodiment

In the present embodiment, a feeling presuming system will be described in which the voice data from the subject is received through a communication network such as the Internet and feeling presumption is performed.

Figure 10:
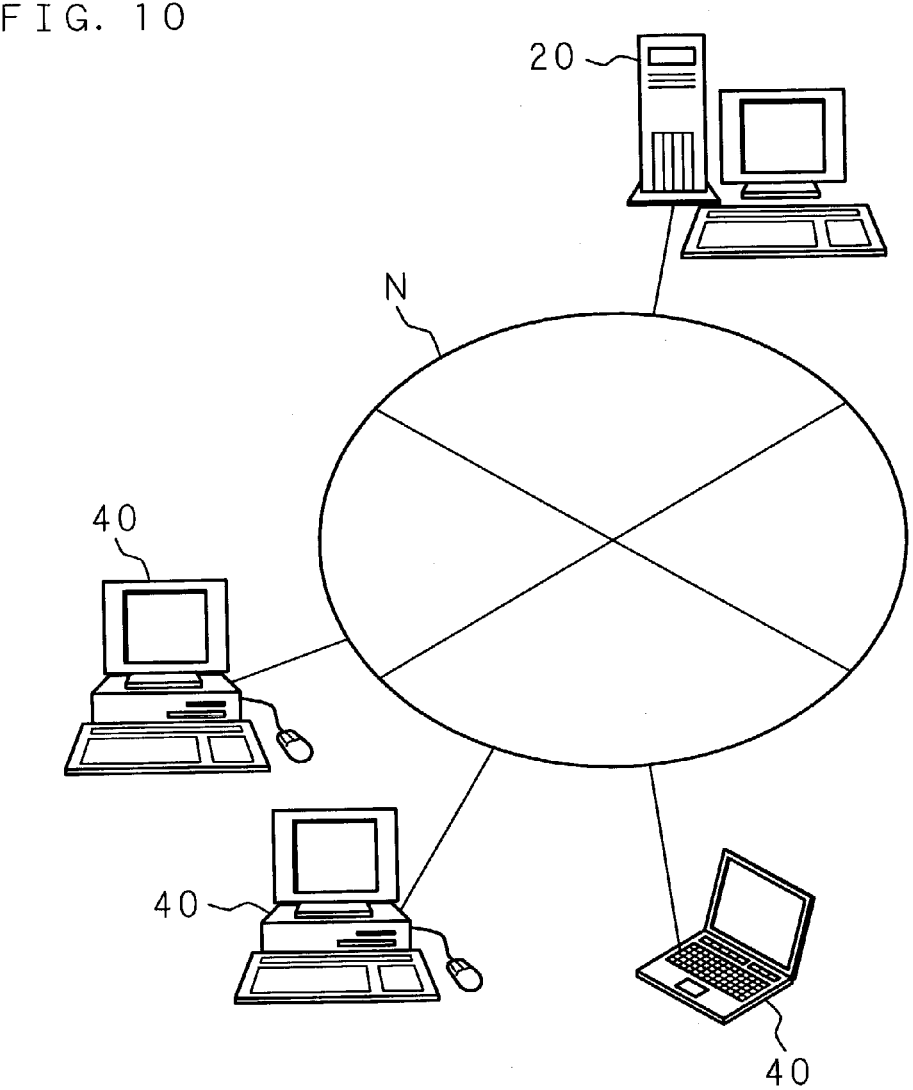
FIG. 10 is a schematic view showing the structure of a feeling presuming system.

FIG. 10 is a schematic view showing the structure of the feeling presuming system of the present embodiment.

The feeling presuming system comprises: an analysis server 20 receiving voice data from the subjects and performing feeling presumption; and information processing apparatuses 40 used by the subjects. The analysis server 20 transmits a web page to the subjects' information processing apparatuses 40 to thereby provide an application for feeling presumption. Since it is necessary to transmit voice data from the subjects' information processing apparatuses 40 when feeling presumption is performed, an RTP (real-time transport protocol) for streaming distribution is set between the analysis server 20 and the subjects' information processing apparatuses 40. When voice data is received by the analysis server 20, the waveform analysis and the voice recognition of the voice data are performed in a manner similar to the above-described one, and feeling presumption is performed.

Figure 11:
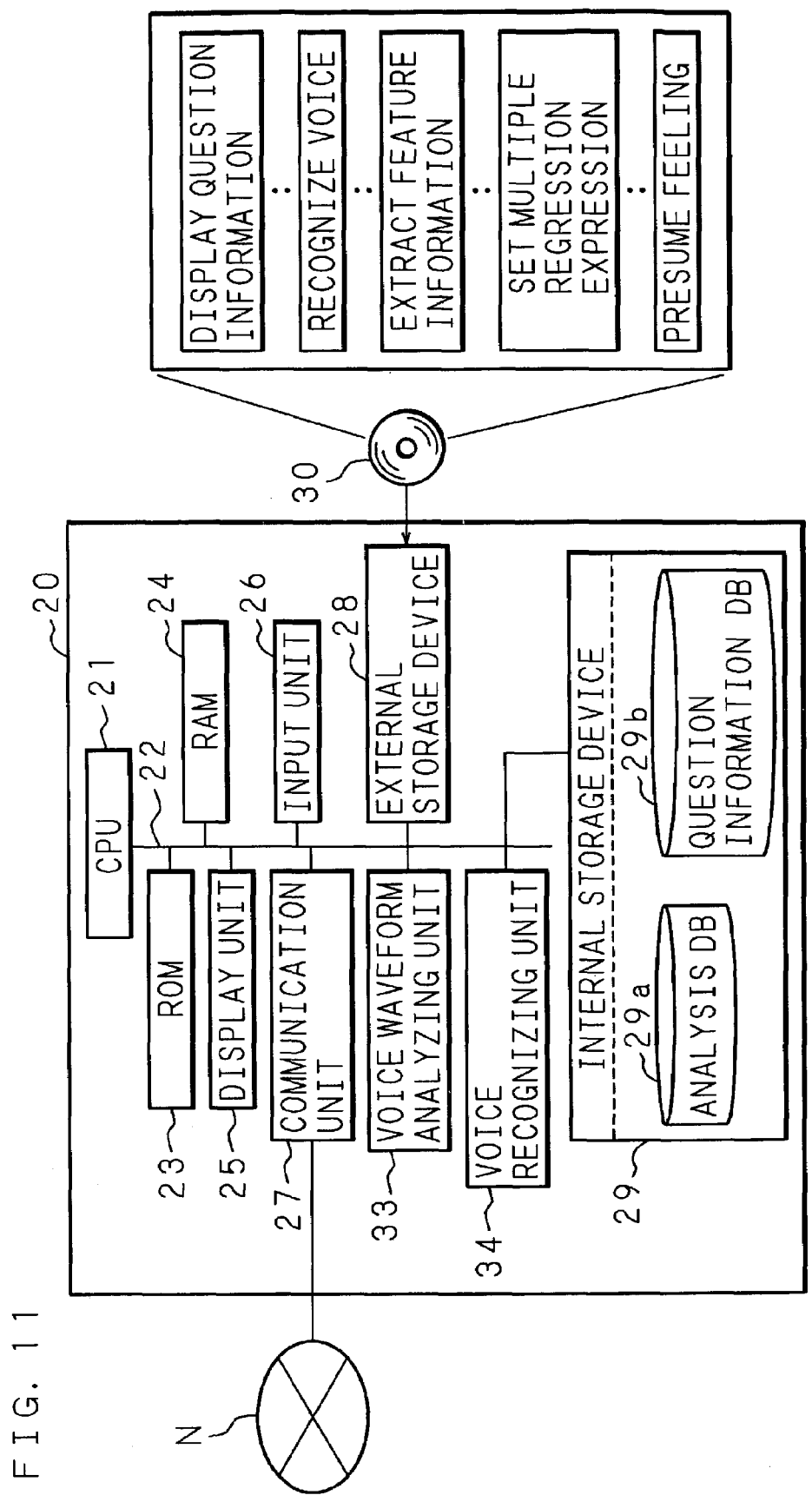
FIG. 11 is a block diagram showing the internal structure of an analysis server.

FIG. 11 is a block diagram showing the internal structure of the analysis server 20. In the figure, reference numeral 21 represents a CPU. The CPU 21 is connected to hardware units described later through a bus 22, and controls the units according to a control program stored in a ROM 23. A RAM 24 comprises an SRAM, a flash memory or the like, and stores data generated when the control program stored in the ROM 23 is executed.

A display unit 25 is a display such as a CRT display or a liquid crystal display. An input unit 26 is an input device such as a keyboard or a mouse. A communication unit 27 is provided with a data circuit-terminating device such as a modem. A web page or the like is transmitted through a communication network N such as the Internet in response to a request from a subject's information processing apparatus 40 to thereby transmit required information to the information processing apparatus 40 and receive voice data from the subject's information processing apparatus 40. The communication unit 27 controls the information transmission and reception. A voice waveform analyzing unit 33 analyzes the waveform of the voice data transmitted from the information processing apparatus 40, and calculates the feature amounts associated with the acoustic features such as the sound pressure, the pitch frequency and the duration.

A voice recognizing unit 34 performs voice recognition on the voice data transmitted from the information processing apparatus 40, and converts the voice information into character string information. The character string information obtained by the conversion is evaluated as described later, and the evaluated value is stored in an analysis database (analysis DB) 29*a*. An internal storage device 29 comprises a storage device such as a hard disk. Part of the storage area thereof is used as: the analysis data base 29*a* storing the feature amounts associated with the acoustic features extracted by analyzing the waveform of the voice data received from the subject's information processing apparatus 40; and a question information database (question information DB) 29*b* storing question information transmitted to the subject's information processing apparatus 40. The internal storage device 29 accesses various databases as required to perform information storage and reading. While various databases are provided in the internal storage device 29 of the analysis server 20 in the present embodiment, these databases are not necessarily provided in the analysis server 20. It may be performed to prepare a database server connected to the analysis server 20 and provide the databases in the database server.

An external storage device 28 comprises a CD-ROM drive or the like reading out a computer program and data from a recording medium 30 such as a CD-ROM on which the computer program and the data of the present invention are recorded. The computer program and the data being read out are stored in the internal storage device 29. The computer program and the data stored in the internal storage device 29 is read into the RAM 24 and executed by the CPU 21, whereby the apparatus operates as the analysis server 20 analyzing the voice data and performing feeling presumption.

Figure 12:
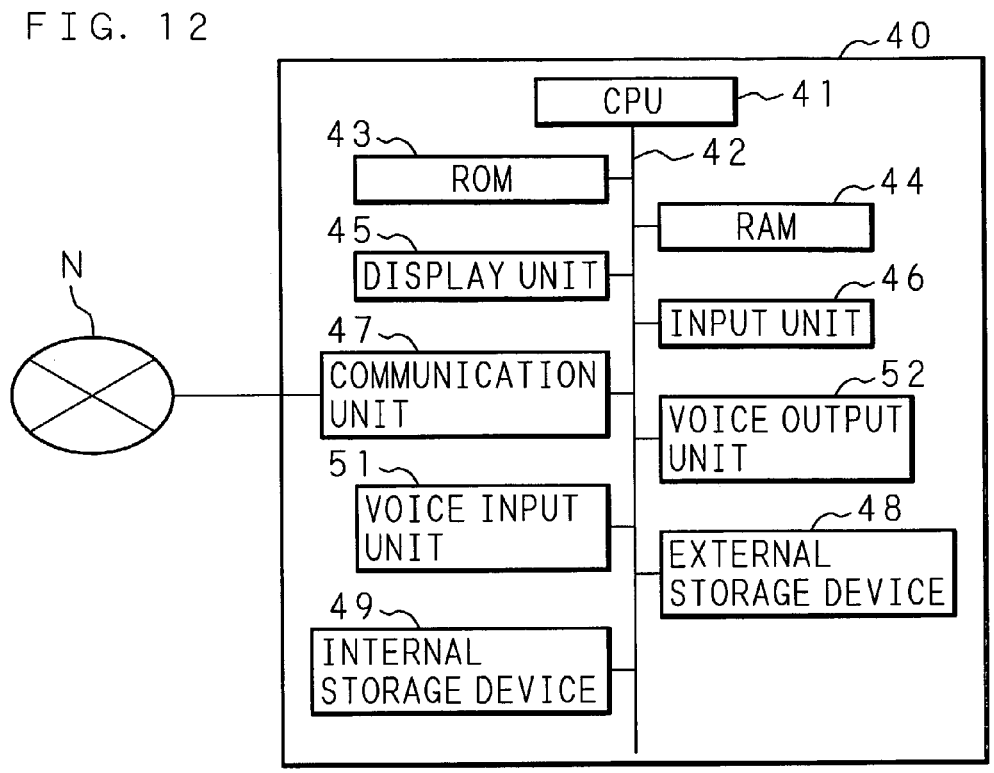
FIG. 12 is a block diagram showing the internal structure of a subject's information processing apparatus.

FIG. 12 is a block diagram showing the internal structure of the subject's information processing apparatus 40. The information processing apparatus 40 is, specifically, a personal computer, and is provided with a CPU 41. The CPU 41 is connected to a ROM 43, a RAM 44, a display unit 45, an input unit 46, a communication unit 47, an external storage device 48 and an internal storage device 49 through a bus 42, and executes a control program stored in the ROM 43 to thereby control the hardware such as the display unit 45 and the input unit 46.

The communication unit 47 is provided with a data circuit-terminating device such as a modem. The communication unit 47 establishes connection with the analysis server 20 through the communication network N, receives a request from the analysis server 20, and transmits necessary information such as voice data. The external storage device 48 comprises a storage device such as a CD-ROM drive. The internal storage device 49 comprises a storage device such as a hard disk. On the internal storage device 49, for example, a web browser or the like for viewing the web page transmitted from the analysis server 20 is installed. A voice input unit 51 is provided with an input device such as a microphone for inputting by voice the answer to the question information transmitted from the analysis server 20. A voice output unit 52 is provided with an output device such as a speaker for outputting by voice the question information transmitted from the analysis server 20.

Figure 13:
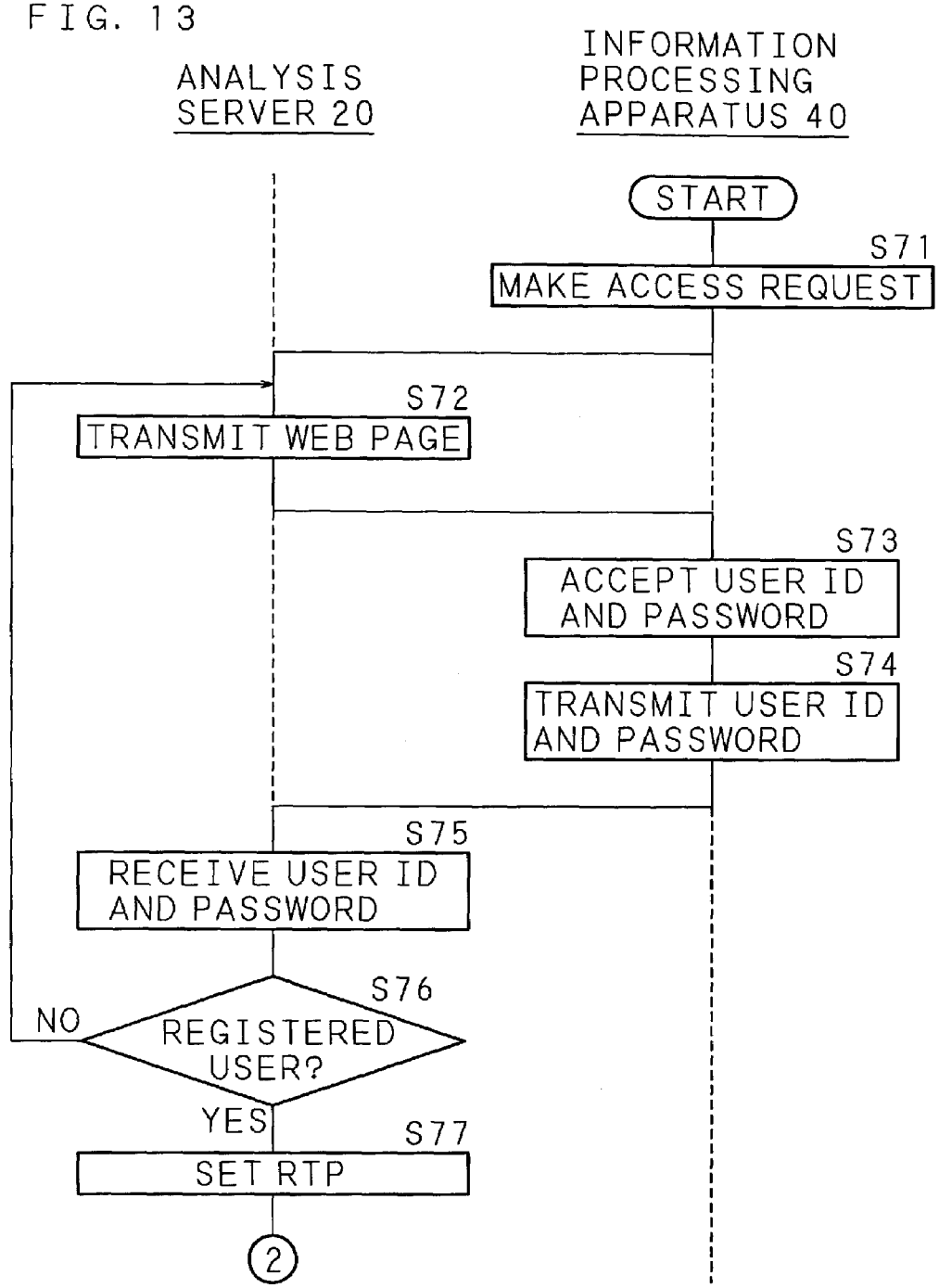
FIG. 13 is a flowchart showing the operation procedure of the feeling presuming system.
Figure 14:
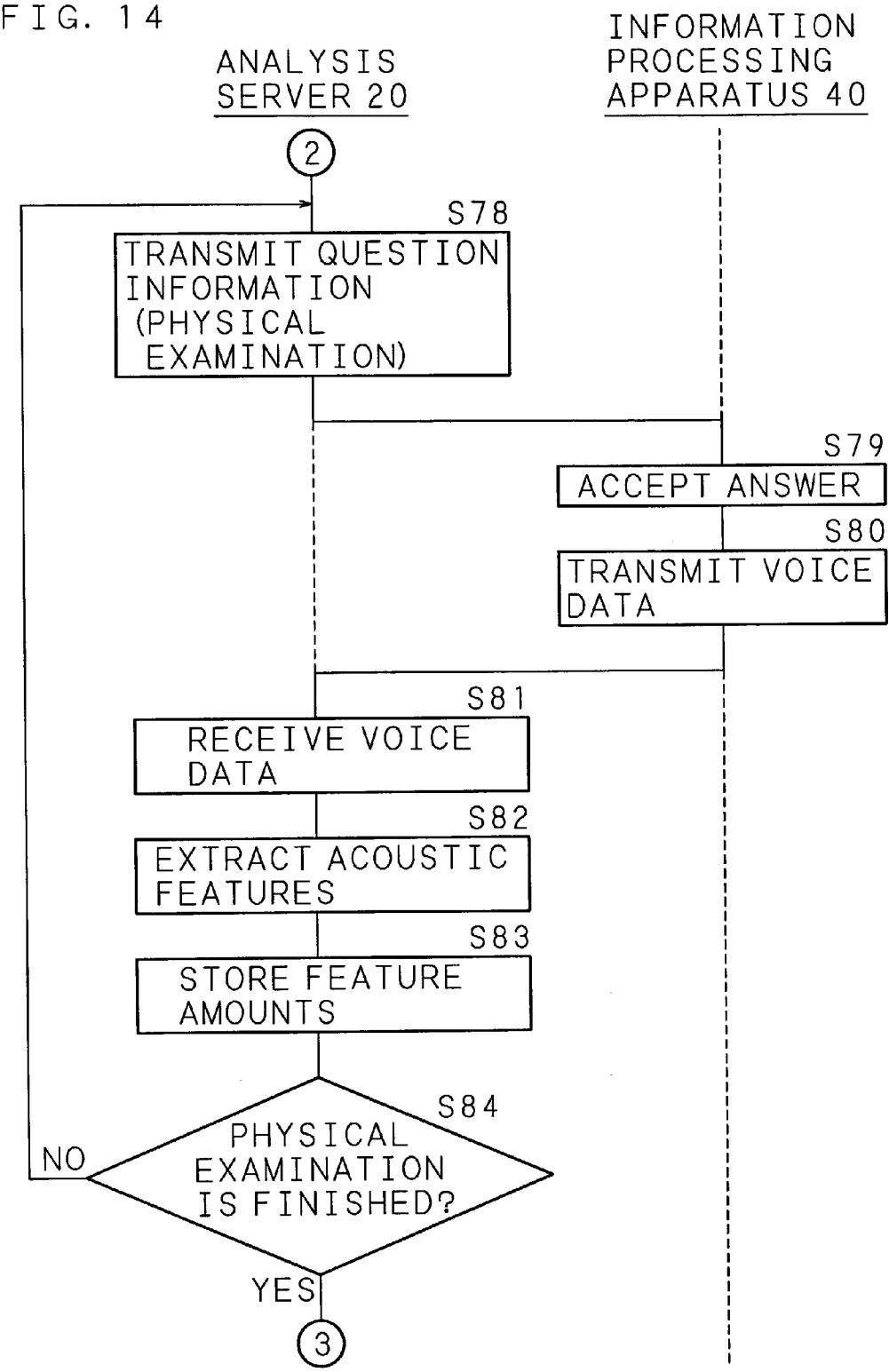
FIG. 14 is a flowchart showing the operation procedure of the feeling presuming system.
Figure 15:
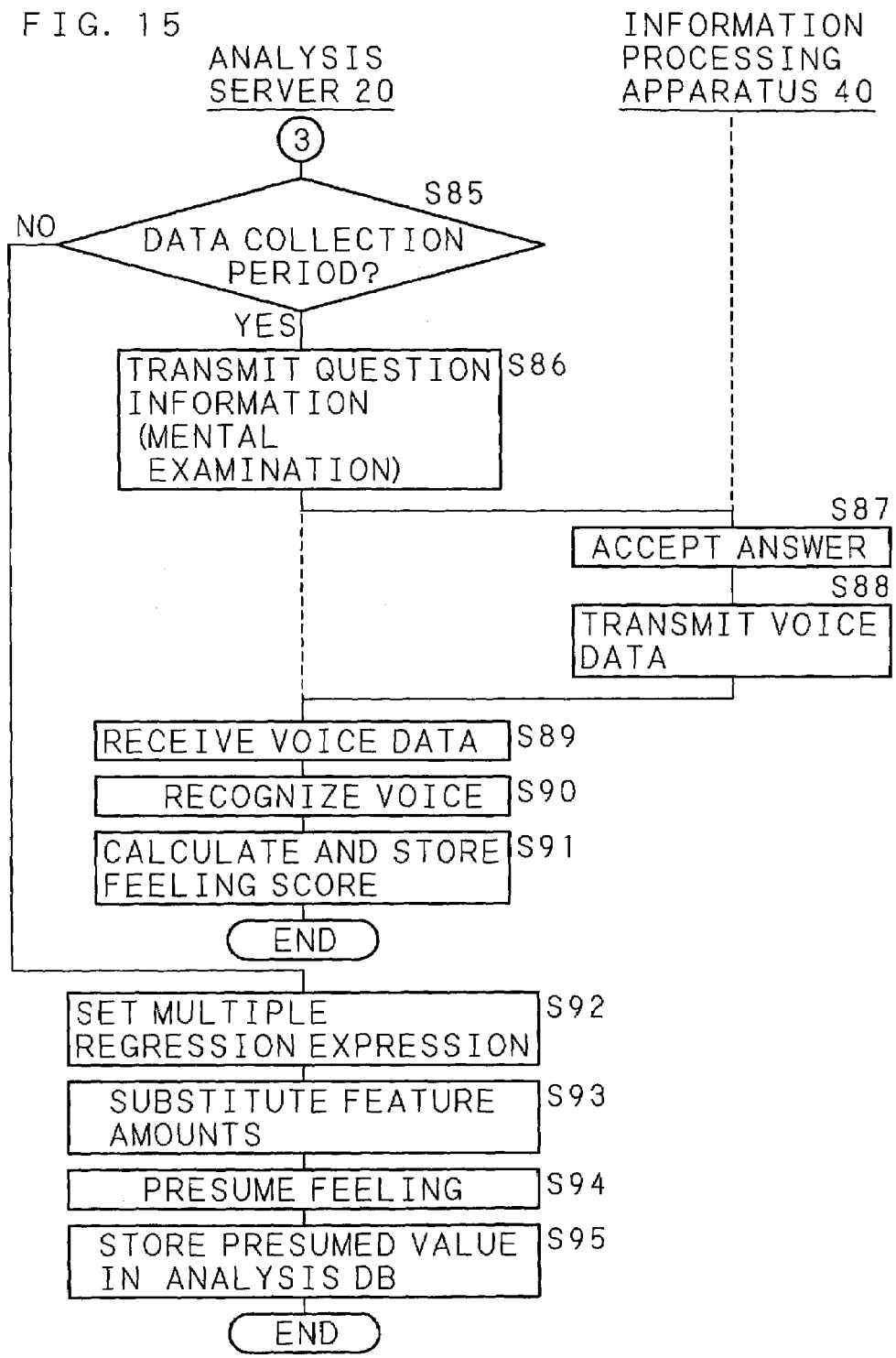
FIG. 15 is a flowchart showing the operation procedure of the feeling presuming system.

FIGS. 13 to 15 are flowcharts showing the processing procedure of the feeling presuming system of the present embodiment. First, in transmitting voice data, the subject inputs a URL or makes an access request to the analysis server 20 by a selection operation from a different web page (step S71). Receiving the access request, the analysis server 20 transmits to the information processing apparatus 40 a web page for inputting the user ID and the password (step S72).

Receiving the web page, the information processing apparatus 40 accepts the input of the user ID and the password (step S73), and transmits the inputted user ID and password to the analysis server 20 (step S74). The analysis server 20 receives the transmitted user ID and password (step S75), and determines whether they are a registered user's or not (step S76). When they are not a registered user's (S76: NO), the process returns to step S72. When they are a registered user's (S76: YES), a protocol (RTP) used in streaming distribution or the like is set (step S77).

Then, the analysis server 20 transmits question information associated with the physical examination by interview (step S78). The question information may be transmitted as character data or may be transmitted as voice data. Receiving the question information, the subject's information processing apparatus 40 accepts answer information (step S79). The answer is accepted by voice, and the voice data associated with the answer inputted through the voice input unit 51 is transmitted to the analysis server 20 (step S80).

The analysis server 20 receives the voice data transmitted from the subject's information processing apparatus 40 (step S81), and extracts the acoustic features of the received voice data (step S82). Then, the analysis server 20 calculates the feature amounts from the extracted acoustic features, and stores them into the analysis database 29a (step S83). Then, the analysis server 20 determines whether the physical examination by interview is finished or not by determining whether the question information associated with the physical examination by interview has all been transmitted or not (step S84). When the physical examination by interview is not finished (S84: NO), the process returns to step S78.

When the question information has all been transmitted and the physical examination by interview is finished (S84: YES), it is determined whether it is the data collection period or not (step S85). When it is the data collection period (S85: YES), question information associated with the mental examination by interview is transmitted to the subject's information processing apparatus 40 (step S86). The question information may be transmitted as character data or may be transmitted as voice data. Receiving the question information, the subject's information processing apparatus 40 accepts answer information (step S87). The answer is accepted by voice, and the voice data associated with the answer inputted through the voice input unit 51 is transmitted to the analysis server 20 (step S88).

The analysis server 20 receives the voice data transmitted from the subject's information processing apparatus 40 (step S89), and performs voice recognition on the received voice data (step S90). Then, the analysis server 20 evaluates the character string extracted by the voice recognition to thereby calculate the feeling score, and stores the calculated feeling score into the analysis database 29a (step S91).

When it is determined at step S85 that it is not the data collection period (S85: NO), the multiple regression expression is set (step S92). When the multiple regression expression is set, the multiple regression analysis is performed by using the sound pressure level, the pitch frequency, the variability with time of the pitch frequency, the duration of the voice and the jitter already stored in the analysis database 29a as explanatory variables and using the feeling score as the objective variable. Then, the feature amounts newly extracted at step S82 are substituted into the set multiple regression expression (step S93), and the presumed value of the feeling score is obtained, thereby performing feeling presumption (step S94). The presumed value of the feeling score is stored into the analysis database 29a (step S95).

Since the answer as voice data is transmitted to the analysis server 20 through the communication network N such as the Internet as described above, the voice data is generally transmitted after compressed. In the present embodiment, since presumption is performed by use of five acoustic features, feeling presumption errors caused by deterioration of the voice data due to compression can be reduced. Also in the present embodiment, the presumed value of the feeling score may be corrected when there is a difference between the feeling score obtained from the answer in the mental examination by interview and the feeling score presumed by the multiple regression analysis. When the feeling is evaluated based on the feeling score, reference values may be set for each subject as mentioned above.

Fifth Embodiment

Figure 16:
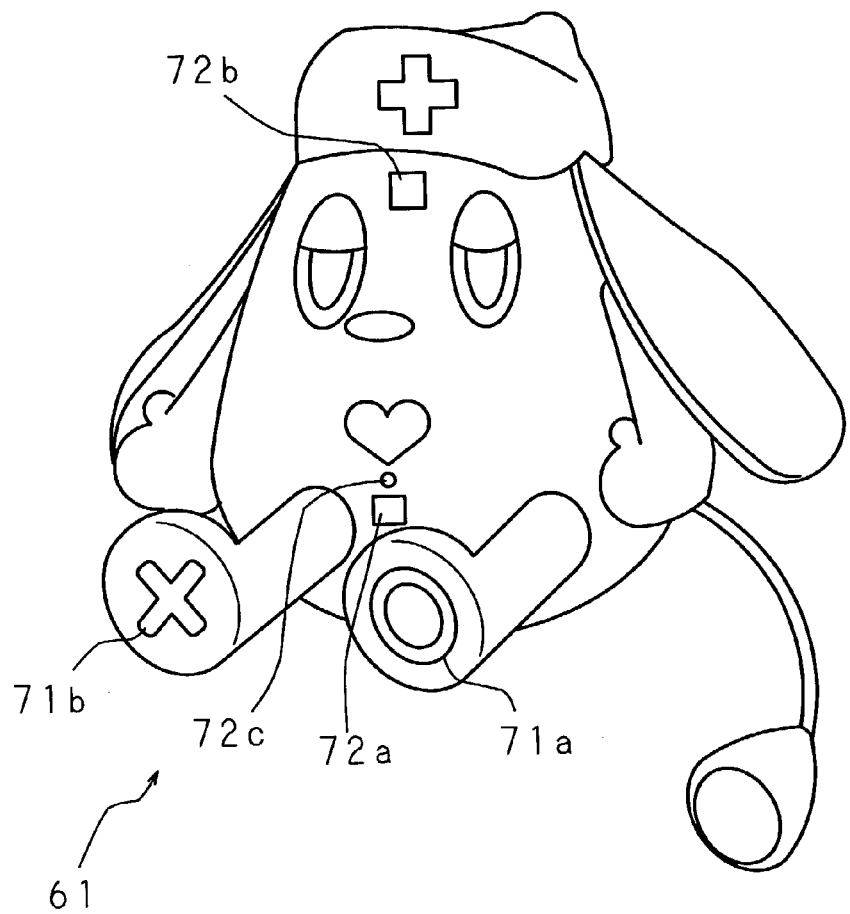
FIG. 16 is a perspective view showing the structure of a relevant part of a health care robot.
Figure 17:
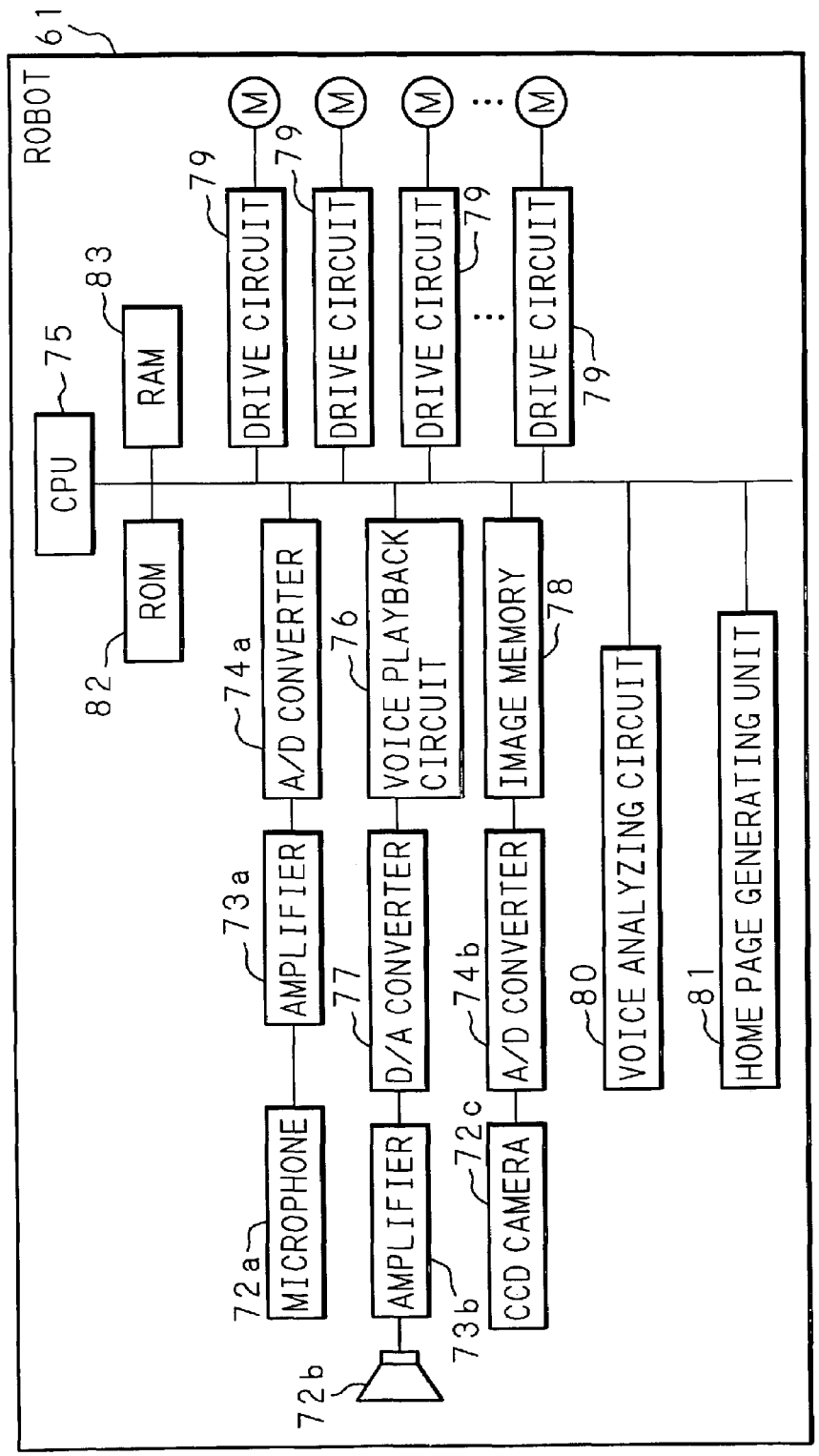
FIG. 17 is a block diagram showing the structure of a relevant part of the health care robot.

FIGS. 16 and 17 are a perspective view and a block diagram each showing the structure of a relevant part of a health care robot 61 (hereinafter, referred simply to robot 61) as an example of the health care terminal apparatus of the present invention, respectively. In the figure, the robot 61 has a body made of plastic, cloth or the like, and has a shape copying after the shape of a pet, an imaginary animal or the like so as to capture the subject's affection. The robot 61 includes an operation mechanism including a plurality of motors M each causing the robot 61 to make a predetermined motion.

A microphone 72a is provided on the front side of the trunk of the robot 61. The microphone 72a is connected to a CPU 75 through an amplifier 73a and an A/D converter 74a. The voice from the subject near the robot 61 is converted into an analog voice signal by the microphone 72a, and the voice signal is amplified by the amplifier 73a. The voice signal outputted from the amplifier 73a is converted into a digital signal by the A/D converter 74a, and supplied to the CPU 75.

A voice playback circuit 76 is connected to the CPU 75. The voice playback circuit 76 includes a ROM storing a plurality of pieces of voice data such as the contents of the questions asked in the medical examination by interview and words encouraging the subject. The voice data will be described later. Voice data is read out from the ROM in response to a control signal outputted from the CPU 75, and a digital voice signal is outputted. The voice playback circuit 76 is connected to a D/A converter 77. The D/A converter 77 is connected to a speaker 72b provided on the front side of the head of the robot 61 through an amplifier 73b. The voice signal outputted from the voice playback circuit 76 is converted into an analog signal by the D/A converter 77, amplified by the amplifier 73b by a predetermined amount, and then, supplied to the speaker 72b to be outputted as an audible sound.

A CCD camera 72c is provided above the microphone 72a on the trunk of the robot 61 so that images of surroundings of the robot 61 are taken. The CCD camera 72c is connected to an A/D converter 74b. The A/D converter 74b is connected to an image memory 78. The image memory 78 is connected to the CPU 75. An image of surroundings is taken by the CCD camera 72c, and the analog signal of the image is outputted from the CCD camera 72c, converted into a digital signal by the AID converter 74b, and stored into the image memory 78 as digital data of the image (image data).

A plurality of drive circuits 79 is connected to the CPU 75, and a motor M is connected to each of the drive circuits 79. In order that the robot 61 makes a predetermined motion, a control signal is outputted from the CPU 75 to the drive circuits 79, and the motors M are driven by the drive circuits 79 based on the control signal.

A voice analyzing circuit 80 analyzing the subject's voice captured through the microphone 72a based on the pitch and the intensity thereof is connected to the CPU 75. Moreover, a home page generating unit 81 generating a home page showing information such as the score of the subject's feeling and the result of the diagnosis of the subject's mental condition as described later is connected to the CPU 75. Further, a ROM 82 storing programs for performing processings described later (the processing of the medical-examination by interview, various processings performed for the subject after the medical examination by interview, etc.) and a RAM 83 storing data temporarily generated when the program of the CPU 75 is executed are connected to the CPU 75.

Figure 18:
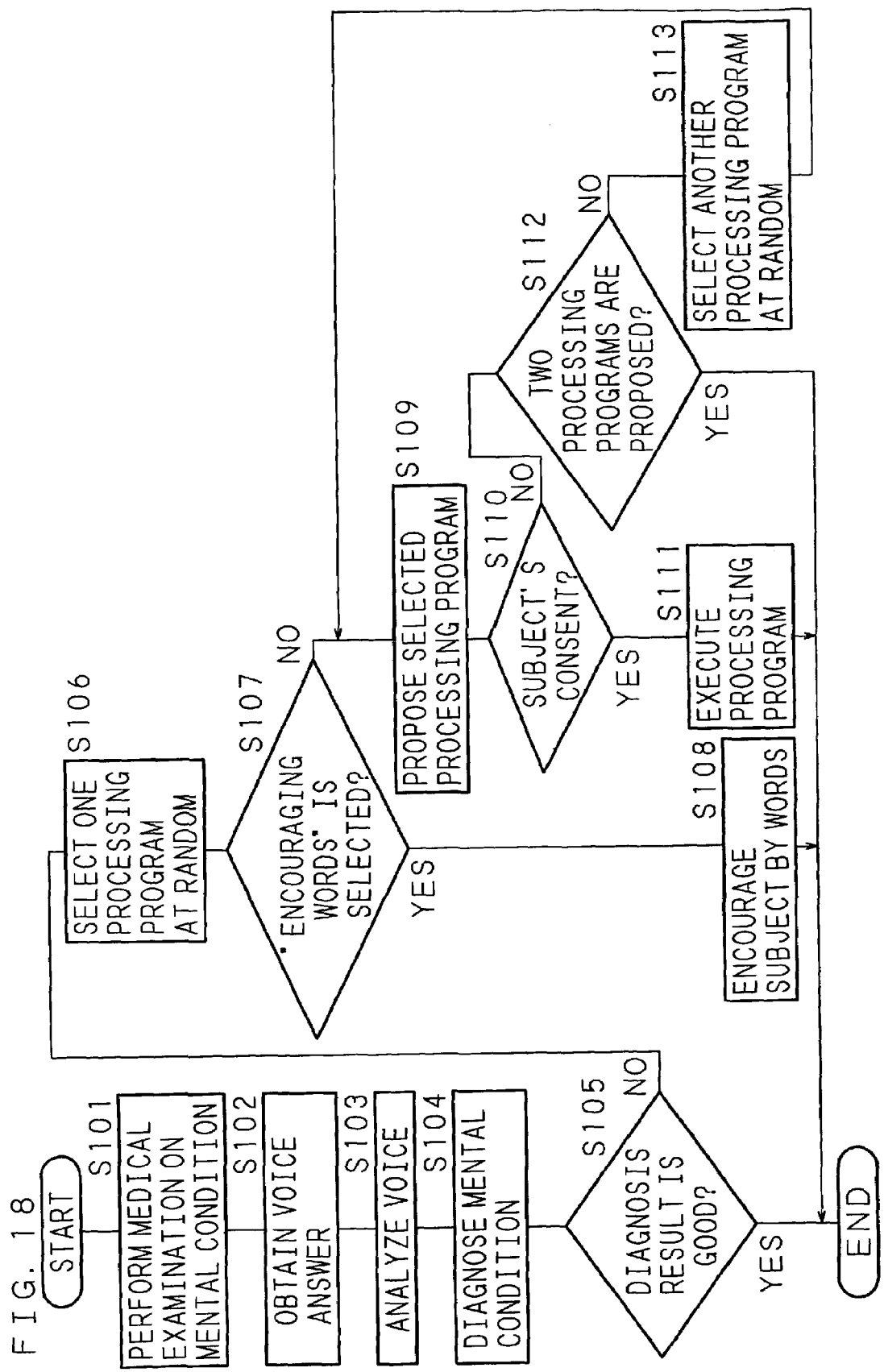
FIG. 18 is a flowchart showing the processing procedure in a CPU of the health care robot.

Next, the operation performed between the subject and the robot 61 which operation uses the robot 61 according to the present invention having the above-described structure will be described. FIG. 18 is a flowchart showing the processing procedure in the CPU 75 of the robot 61.

First, the CPU 75 performs a medical examination by interview on the subject's mental condition (step S101). Specifically, the CPU 75 outputs a control signal to the voice playback circuit 76, and causes a voice "What is the score of your feeling today when the best feeling is rated as 100?" to be outputted from the speaker 72b.

The CPU 75 obtains an answer by voice from the subject in the mental examination by interview through the microphone 72a (step S102). The voice analyzing circuit 80 analyzes the subject's current mental condition with reference to the pitch and the intensity of the inputted voice (step S103), and transmits the result of the analysis to the CPU 75. The CPU 75 diagnoses the subject's mental condition based on the contents of the subject's answer (the feeling score) and the result of the analysis (step S104).

While a mental examination by interview making the subject to reply with the feeling score is performed in the above-described example, unlike this, it may be performed to preset a plurality of items (GHQ, self-esteem scale, etc.) to be asked and make the subject to answer the question items by selecting either a "◯" mark 71a or a "×" mark 71b of the robot 61. In this case, the answer is expressed by a score and the score is used as the contents of the answer (feeling score). The subject may answer these question items by voice such as "Yes/No." Further, the subject may answer these question items by touching his selection on a touch panel.

The CPU 75 determines whether the result of the diagnosis is good or not (step S105). When it is good (S105: YES), the operation ends. When the mental condition is not good (S105: NO), the CPU 75 selects one processing program at random from among the processing programs stored in the ROM 82 (step S106). These processing programs are broadly divided into two kinds. One kind is to provide the subject with "encouraging words" and the other is to propose a certain processing. The former kind of processing programs are executed without the subject's consent, and the latter kind of processing programs are executed after the proposal is accepted by the subject.

The CPU 75 determines the contents of the selection (step S107). When the provision of "encouraging words" is selected (S107: YES), the CPU 75 selects one or a plurality of encouraging words from among a plurality of "encouraging words" stored in a ROM of the voice playback circuit 76, and outputs the words through the speaker 72b by voice (step S108). As these "encouraging words," for example, "Are you okay?," "Cheer up.," "What's wrong?," and "Go for it!" are used.

When a processing program other than the processing programs to provide "encouraging words" is selected (S107: NO), the CPU 75 proposes the processing program to the subject with a voice output through the speaker 72b (step S109). Then, the CPU 75 determines whether the subject consents to the proposal or not based on the voice input representative of the presence or absence of the subject's consent through the microphone 72a (step S110). When a voice representative of the subject's consent is recognized (S110: YES), the CPU 75 executes the processing program for the subject (step S111).

Concrete examples of the proposal and execution of these processing programs include the following:

(1) Performing Ten-Second Breathing

First, a proposal "How about performing ten-second deep breathing?" is made to the subject, and after the subject makes an answer of consent "Yes," ten-second breathing for relaxation is executed according to a predetermined voice guide.

(2) Playing Back a Voice Memo

A talk (for example, "I love you.", or "Play with me again.") from a grandchild of the subject's is previously recorded. A proposal "How about listening to (the grandchild's name)'s voice?" is made to the subject, and after the subject makes an answer of consent "Yes," the recorded voice is played back.

(3) Playing a Game

For example, a proposal "Shall we play a word-chain game?" is made to the subject, and after the subject makes an answer of consent "Yes," a word-chain game is played between the subject and the robot 16. In addition to the "word-chain game," games such as "fortune-telling" and "paper-rock-scissors" can be selected.

(4) Playing Back Body Data

For example, a proposal "Shall I inform you of your recent blood pressure values?" is made to the subject, and after making an answer of consent "Yes," the subject is informed of the recent transition of his blood pressure value, and a comment on the transition such that "Your blood pressure is rather high for these three days." is also outputted by voice.

(5) Recording the Mental Condition onto a Doctor's Terminal

For example, a proposal "Shall I inform Dr. B of your today's mental condition?" is made to the subject, and after the subject makes an answer of consent "Yes," the feeling score told by the subject in the mental examination by interview or the mental condition as a result of the diagnosis is transmitted to the doctor's terminal.

When the subject's voice expressing nonconsent to one of the above-described processing programs (1) to (5) proposed by the robot 61 is recognized (S110: NO), the CPU 75 determines whether two processing programs have already been proposed or not (step S112).

When only one processing program has been proposed (S112: NO), the CPU 75 selects a processing program different from the previously proposed one at random (step S113). Then, the CPU 75 proposes the selected processing program to the subject by voice outputted through the speaker 72b (S109). When a voice expressing consent is recognized (S110: YES), the processing program is executed for the subject (S111). When two processing programs have already been selected at random (S112: YES), the process ends without making any more proposal.

According to the present invention, since processing programs can be selected at random, the subject always responds with a fresh feeling, so that the subject can be prevented from losing interest. Moreover, since the processing programs other than the processing programs to provide "encouraging words" are executed after the subject's consent to the proposal is obtained, measures reflecting the subject's intention can be taken. Moreover, since the proposal of the processing program is made not more than twice, the proposal is never made persistently, so that the subject never dislikes the system.

Although no processing program is executed when the subject's mental condition is good in the above-described example, it is considered that the subject loses interest if this is always done. Therefore, by sometimes performing a processing program selected at random even when the mental condition is good like when the mental condition is not good, the subject can be prevented from losing interest. Moreover, whether to perform a selected processing program even when the mental condition is good or not is determined at random.

It may be performed to store the historical information (frequency of use) of the processing programs which the subject has consented to execute so that a processing program which the subject uses by preference is selected with priority with reference to the historical information in selecting a processing program.

Next, the operation processing in the home page generating unit 81 will be described. The home page generating unit 81 generates a home page showing information on the subject's mental condition. FIG. 19 is a view showing an example of the home page. On the home page, the following are written: the date of the mental examination by interview; the score of the subject's feeling in the mental examination by interview; the contents of the processing program performed after the mental examination by interview; the feeling of the robot 61; and the score provided by the robot 61.

The feeling of the robot 61 is a comment of the robot 61 based on the result of the diagnosis of the subject's mental condition. Examples other than the ones shown in FIG. 19 include "I wonder if you(the subject) are okay," "The score is higher than yesterday.," and "Were you(the subject) angry?."

The score provided by the robot 61 is calculated from a reference value and the complementary variable of that day. The reference value is determined every day by combining two dimensions of pleasant-unpleasant and activation-deactivation as sinusoidal waves having different periods. The complementary variable is determined with reference to, for example, the score of the subject's feeling in the mental examination by interview, the state of charge of the robot 61, the room temperature, the humidity and the number of times of reaction at a sensor sensing that a person is near by, based on the following:

the feeling score→added when the score is high;
the state of charge→added when the battery is in good condition;
the room temperature→added when the temperature is in a comfortable range;
the humidity→added when the humidity is in a comfortable range; and
the sensor→added when the subject is near the robot 61 and the number of times of reaction is large.

As described above, according to the present invention, a home page is generated showing information on the subject's mental condition such as the contents of the subject's answer in the mental examination by interview and the result of the diagnosis of the subject's mental condition, the subject's relatives and the like living far away can be easily informed of the user's mental health condition.

For subjects who do not want to make their own information open, it is possible to limit the right of access to the home page to themselves so that others cannot view the information. In this case, since the subject and the robot 61 share the information as a secret between them, the intimacy between the subject and the robot 61 increases.

While a home page showing information on the subject's mental condition is generated in the robot 61 in the above-described example, information as mentioned above may be supplied from the robot 61 to the server so that the home page is generated on the server. Moreover, it is to be noted that the above-mentioned items shown on the home page are merely examples, and the items are not limited to the examples.

Figure 20:
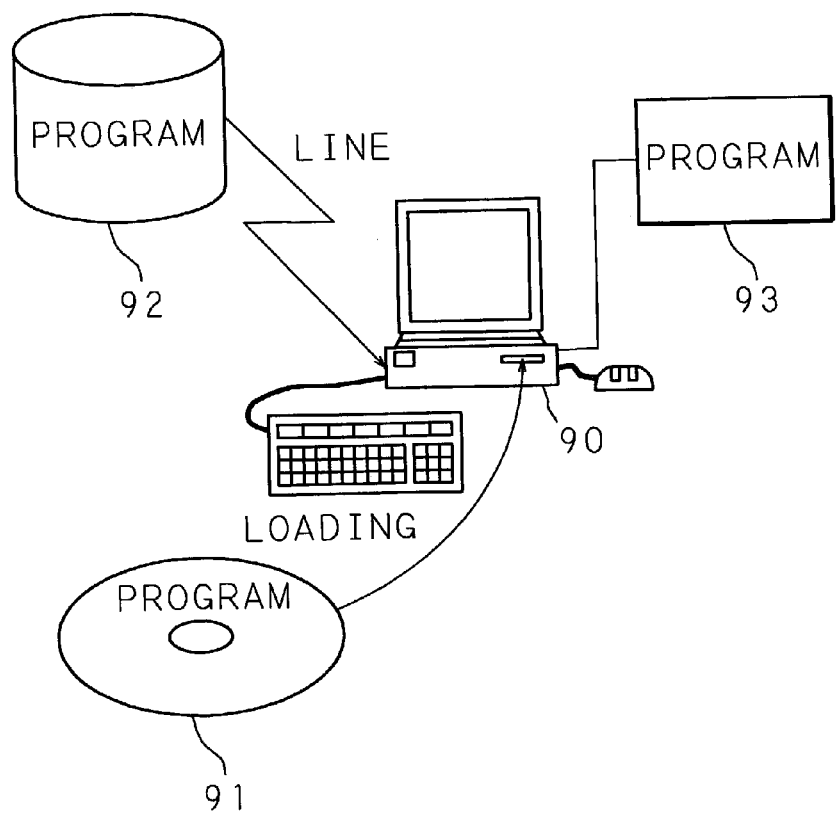
FIG. 20 is a schematic view showing a hardware structure in a case where a personal computer is used.

While a case is described in which with the health care terminal apparatus as the robot 61, interactive processing is performed between the robot 61 and the subject, the present invention is not limited thereto. It is possible to load a computer program for performing the above-described processing from a recording medium or the like onto a personal computer and perform a similar processing between the personal computer and the subject. FIG. 20 is a schematic view showing a hardware structure in such a case. A personal computer 90 loads a computer program for performing the above-described processing from a recording medium such as a portable recording medium 91 such as a magnetic disk or a CD-ROM, a memory 92 on the other end of the line capable of wireless or wire program communication with the personal computer 90 and provided, for example, in the center of a medical institution, or a memory 93 on the side of the processing apparatus such as a RAM or a hard disk provided in the personal computer 90.

As described above in detail, according to the present invention, a medical examination by interview on the subject's mental condition is performed, the subject's mental condition is diagnosed based on the subject's answer, one processing program is selected from among a plurality of prepared processing programs, and the selected processing program is executed, so that an appropriate processing can be performed in accordance with the subject's mental condition, whereby the subject's mental health condition can be improved.

Moreover, according to the present invention, since the processing program executed for the subject is selected at random, the subject always finds something fresh and never loses interest, so that health care can be continued over a long period of time.

Further, according to the present invention, voice analysis is performed on the subject's answer in the medical examination by interview and the subject's mental condition is diagnosed based on the result of the analysis and the contents of the answer in the medical examination by interview, so that the subject's mental condition can be more precisely diagnosed.

As this invention may be embodied in several forms without departing from the spirit of essential characteristics thereof, the present embodiment is therefore illustrative and not restrictive, since the scope of the invention is defined by the appended claims rather than by the description preceding them, and all changes that fall within metes and bounds of the claims, or equivalence of such metes and bounds thereof are therefore intended to be embraced by the claims.

The invention claimed is:

1. An information processing method comprising the steps of:
    outputting, from an output unit, a first piece of question information and a second piece of question information previously stored in a storing unit and correlated with each other;
    accepting answers to the outputted first and second pieces of question information by voice;

extracting character string information from a voice associated with the accepted answer to the first piece of question information;

extracting at least one piece of feature information associated with the acoustic features from a voice associated with the accepted answer to the second piece of question information;

storing the extracted character string information and feature information so as to be associated with each other;

setting a correlation between the stored character string information and feature information; and identifying, when a voice associated with an answer to the second piece of question information is newly accepted by said accepting unit, character string information correlated with at least one piece of feature information associated with the acoustic features extracted from the accepted voice, based on the piece of feature information and the set correlation.

2. An information processing method according to claim 1, wherein one of the first and the second pieces of question information is question information on a mental condition and the other of the first and the second pieces of question information is question information on a physical condition.

3. An information processing method according to claim 1, further comprising the steps of:

when the answer to the first or the second piece of question information is accepted by voice, determining whether the answer was accepted during a predetermined period; and if the answer was accepted during the predetermined period, setting the correlation between the stored character string information and feature information.

4. An information processing method according to claim 1, further comprising the steps of:

calculating a feature amount characterizing each of the stored character string information and feature information;

using multivariate analysis on the calculated feature amounts; and setting the correlation based on the analyzed feature amounts.

5. The information processing method according to claim 1, wherein the step of extracting at least one piece of feature information associated with the acoustic features from a voice associated with the accepted answer to the second piece of question information comprises the step of:

extracting at least one of a sound pressure, a pitch frequency, and a duration of the voice associated with the accepted answer to the second piece of question information.

6. An information processing system comprising:

a first storing unit configured to store question information;

a first output unit configured to output the question information stored in said first storing unit;

a first accepting unit configured to accept a voice, in which an answer to the question information outputted from said first output unit is accepted by voice, and information accompanying the accepted voice is presumed based on acoustic features extracted from the accepted voice;

a second output unit configured to output a first piece of question information and a second piece of question information previously stored in said first storing unit and correlated with each other;

a second accepting unit configured to accept answers to the outputted first and second pieces of question information by voice;

a character string information extracting unit configured to extract character string information from a voice associated with the accepted answer to the first piece of question information;

a feature information extracting unit configured to extract at least one piece of feature information associated with the acoustic features from a voice associated with the accepted answer to the second piece of question information;

a second storing unit configured to store the extracted character string information and feature information so as to be associated with each other; and a setting unit configured to set a correlation between the stored character string information and feature information, wherein when a voice associated with an answer to the second piece of question information is newly accepted by said second accepting unit, character string information correlated with at least one piece of feature information associated with the acoustic features extracted from the accepted voice is identified based on the piece of feature information and the set correlation.

7. An information processing system according to claim 6, wherein one of the first and the second pieces of question information is question information on a mental condition and the other of the first and the second pieces of question information is question information on a physical condition.

8. An information processing system according to claim 6, further comprising:

a determining unit configured to determine whether the answer to the first or the second piece of question information accepted by voice has been accepted during a predetermined period, and further configured to set the correlation between the stored character string information and feature information if the answer has been accepted during the predetermined period.

9. An information processing system according to claim 6, further comprising:

a calculation unit configured to calculate a feature amount characterizing each of the stored character string information and feature information, and further configured to calculate a multivariate analysis of the feature amounts; and a correlation unit configured to set the correlation using the calculated multivariate analysis of the feature amounts.

10. An information processing system comprising:

a first information processing apparatus, said first information processing apparatus comprising:

a first storing unit configured to store question information; and a first transmitting unit configured to transmit the question information stored in said first storing unit; and a second information processing apparatus connected to the first information processing apparatus through a communication network, said second information processing apparatus comprising:

a first receiving unit configured to receive question information transmitted through the communication network;

a first accepting unit configured to accept an answer to the received question information by voice; and a second transmitting unit configured to transmit voice information associated with the accepted voice;

wherein said first information processing apparatus is configured to presume information accompanying the voice information received through the communication network based on acoustic features extracted from the voice information, wherein said second information processing apparatus further comprises:

a second receiving unit configured to receive, through the network, a first piece of question information and a second piece of question information previously stored in said first storing unit of said first information processing apparatus and correlated with each other;

a first output unit configured to output the received first and second pieces of question information;

a second accepting unit configured to accept answers to the outputted first and second pieces of question information by voice; and a third transmitting unit configured to transmit voice information associated with the accepted voice, wherein said first information processing apparatus further comprises:

a character string information extracting unit configured to extract character string information from voice information associated with the received answer to the first piece of question information;

a feature information extracting unit configured to extract at least one piece of feature information associated with the acoustic features from voice information associated with the received answer to the second piece of question information;

a second storing unit configured to store the extracted character string information and feature information so as to be associated with each other; and a setting unit configured to set a correlation between the stored character string information and feature information, and wherein when voice information associated with an answer to the second piece of question information is newly received from said second information processing apparatus, character string information correlated with at least one piece of features information associated with the acoustic features extracted from the received voice information is identified based on the piece of feature information and the set correlation.

11. An information processing system according to claim 10, wherein one of the first and the second pieces of question information is question information on a mental condition and the other of the first and the second pieces of question information is question information on a physical condition.

12. An information processing system according to claim 10, further comprising:

a determining unit configured to determine whether the answer to the first or the second piece of question information accepted by voice has been accepted during a predetermined period, and further configured to set the correlation between the stored character string information and feature information if the answer has been accepted during the predetermined period.

13. An information processing system according to claim 10, further comprising:

a calculation unit configured to calculate a feature amount characterizing each of the stored character string information and feature information, and further configured to calculate a multivariate analysis of the feature amounts; and a correlation unit configured to set the correlation using the calculated multivariate analysis of the feature amounts.

14. An information processing apparatus comprising:

a first storing unit configured to store question information;

a first output unit configured to output the question information stored in said first storing unit;

a first accepting unit configured to accept a voice, in which an answer to the question information outputted from said first output unit is accepted by voice, and information accompanying the accepted voice is presumed based on acoustic features extracted from the accepted voice;

a second output unit configured to output a first piece of question information and a second piece of question information previously stored in said first storing unit and correlated with each other;

a second accepting unit configured to accept answers to the outputted first and second pieces of question information by voice;

a character string information extracting unit configured to extract character string information from a voice associated with the accepted answer to the first piece of question information;

a feature information extracting unit configured to extract at least one piece of feature information associated with the acoustic features from a voice associated with the accepted answer to the second piece of question information;

a second storing unit configured to store the extracted character string information and feature information so as to be associated with each other; and a setting unit configured to set a correlation between the stored character string information and feature information, wherein when a voice associated with an answer to the second piece of question information is newly accepted by said second accepting unit, character string information correlated with at least one piece of feature information associated with the acoustic features extracted from the accepted voice is identified based on the piece of feature information and the set correlation.

15. An information processing apparatus according to claim 14, wherein one of the first and the second pieces of question information is question information on a mental condition and the other of the first and the second pieces of question information is question information on a physical condition.

16. An information processing apparatus according to claim 14, further comprising:

a determining unit configured to determine whether the answer to the first or the second piece of question information accepted by voice has been accepted during a predetermined period, and further configured to set the correlation between the stored character string information and feature information if the answer has been accepted during the predetermined period.

17. An information processing apparatus according to claim 14, further comprising:

a calculation unit configured to calculate a feature amount characterizing each of the stored character string information and feature information, and further configured to calculate a multivariate analysis of the feature amounts; and a correlation unit configured to set the correlation using the calculated multivariate analysis of the feature amounts.

18. An information processing apparatus according to claim 14, wherein said feature information extracting unit comprises at least one of:
   a detecting unit configured to detect a sound pressure of inputted voice information;
   a detecting unit configured to detect a pitch frequency of the inputted voice information;
   a detecting unit configured to detect duration of the inputted voice information; and
   a detecting unit configured to detect jitter of the inputted voice information.

19. An information processing apparatus according to claim 14, further comprising:
   a third output unit configured to output appropriate information in accordance with the identified character string information.

20. An information processing apparatus being connectable to a communication network, said information processing apparatus comprising:
a first receiving unit configured to receive voice information, and further configured to presume information accompanying the received voice information based on acoustic features extracted from the received voice information;
   a second receiving unit configured to receive answers to a first piece of question information and a second piece of question information correlated with each other as voice information though the communication network;
   a character string information extracting unit configured to receive character string information included in the voice information associated with the received answer to the first piece of question information from the voice information;
   a feature information extracting unit configured to extract at least one piece of feature information associated with the acoustic features from voice information associated with the received answer to the second piece of question information;
   a storing unit configured to extract the extracted character string information and feature information so as to be associated with each other; and
   a setting unit configured to set a correlation between the stored character string information and feature information,
   wherein when voice information associated with an answer to the second piece of question information is newly received, character string information correlated with at least one piece of feature information associated with the acoustic features extracted from the received voice information is identified based on the piece of feature information and the set correlation.

21. An information processing apparatus according to claim 20, wherein one of the first and the second pieces of question information is question information on a mental condition and the other of the first and the second pieces of question information is question information on a physical condition.

22. An information processing apparatus according to claim 20, further comprising:
a determining unit configured to determine whether the answer to the first or the second piece of question information accepted by voice has been accepted during a predetermined period, and further configured to set the correlation between the stored character string information and feature information if the answer has been accepted during the predetermined period.

23. An information processing apparatus according to claim 20, further comprising:
   a calculation unit configured to calculate a feature amount characterizing each of the stored character string information and feature information, and further configured to calculate a multivariate analysis of the feature amounts; and
   a correlation unit configured to set the correlation using the calculated multivariate analysis of the feature amounts.

24. An information processing apparatus according to claim 20, wherein said feature information extracting unit comprises at least one of:
   a detecting unit configured to detect a sound pressure of inputted voice information;
   a detecting unit configured to detect a pitch frequency of the inputted voice information;
   a detecting unit configured to detect duration of the inputted voice information; and
   a detecting unit configured to detect jitter of the inputted voice information.

25. An information processing apparatus according to claim 20, further comprising:
   a third output unit configured to output appropriate information in accordance with the identified character string information.

26. A computer-readable recording medium on which a computer program is recorded that causes a computer to extract acoustic features associated with inputted voice information and presume information accompanying the voice information based on the extracted acoustic features, wherein the computer program is configured to perform:
   a step of causing the computer to output a first piece of question information and a second piece of question information correlated with each other;
   a step of causing the computer to accept answers to the outputted first and second pieces of question information by voice information;
   a step of causing the computer to extract character string information from the voice information associated with the accepted answer to the first piece of question information;
   a step of causing the computer to extract at least one piece of feature information associated with the acoustic features from the voice information associated with the accepted answer to the second piece of question information;
   a step of causing the computer to store the extracted character string information and feature information so as to be associated with each other;
   a step of causing the computer to set a correlation between the stored character string information and feature information; and
   a step of causing the computer to identify, when voice information associated with an answer to the second piece of question information is newly accepted, character string information correlated with at least one piece of feature information associated with the acoustic features extracted from the accepted voice information, based on the piece of feature information and the set correlation.

* * * * *